United States Patent [19]

Uhr et al.

[11] Patent Number: 5,686,072
[45] Date of Patent: Nov. 11, 1997

[54] EPITOPE-SPECIFIC MONOCLONAL ANTIBODIES AND IMMUNOTOXINS AND USES THEREOF

[75] Inventors: Jonathan W. Uhr; Ellen S. Vitetta, both of Dallas; Richard H. Scheuermann, Carrollton, all of Tex.

[73] Assignee: Board of Regents, The University of Texas, Austin, Tex.

[21] Appl. No.: 202,042

[22] Filed: Feb. 22, 1994

Related U.S. Application Data

[63] Continuation-in-part of Ser. No. 899,781, Jun. 17, 1992, abandoned.

[51] Int. Cl.[6] .................................................. A61K 39/395
[52] U.S. Cl. ........................... 424/183.1; 530/391.7; 530/388.73; 435/7.24
[58] Field of Search ............... 424/183.1; 530/391.7, 530/388.73; 435/7.24

[56] References Cited

U.S. PATENT DOCUMENTS

| | | |
|---|---|---|
| 4,664,911 | 5/1987 | Uhr et al. |
| 4,689,311 | 8/1987 | Weltman |
| 4,831,117 | 5/1989 | Uckun |
| 4,925,922 | 5/1990 | Byers et al. |
| 5,045,451 | 9/1991 | Uhr et al. |

OTHER PUBLICATIONS

Canevari et al., Ann Oncol., vol. 5/8, pp. 698–701 1994.
Seaver, Gentic Engineering News, pp. 10 and 21, (1994).
Hermentin et al., Behring Inst. Mitt, No. 82, pp. 197–215 1988.
Rigley et al., Eur. J. Immunol., vol. 21, pp. 535–540, (1991).
Campana, D. et al., "Human B Cell Development I. Phenotypic Differences of B Lymphocytes in the Bone Marrow and Peripheral Lymphoid Tissue," *The Journal of Immunology*, 134(3):1524–1530, 1985.
Fulton, R. J. et al., "In Vivo Therapy of the BCL Tumor: Effect of Immunotoxin Valency and Deglycosylation of the Ricin A Chain," *Cancer Research*, 48:2626–2631, 1988.
Ghetie, M. et al., "Antitumor Activity of Fab' and IgG–anti–CD22 Immunotoxins in Disseminated Human B Lymphoma Grown in Mice with Severe Combined Immunodeficiency Disease: Effect on Tumor Cells in Extranodal Sites," *Cancer Research*, 51:5876–5880, 1991.
Ghetie, M. et al., "Evaluation of Ricin A Chain–containing Immunotoxins Directed against CD19 and CD22 Antigens on Normal and Malignant Human B–Cells as Potential Reagents for in Vivo Therapy," *Cancer Research*, 48:2610–2617, 1988.
Ghetie, V. et al., "Large Scale Preparation of Immunotoxins Constructed with the Fab' Fragment of IgG1 Murine Monoclonal Antibodies and Chemically Deglycosylated Ricin A Chain," *Journal of Immunological Methods*, 112:267–277, 1988.

Katz, F. E. et al., "Elimination of T Cells From Human Peripheral Blood and Bone Marrow Using A Cocktail of Three Anti–T Cell Immunotoxins," *British Journal of Haematology*, 67:407–411, 1987.

Li, J. et al., "The Epitope Specificity and Tissue Reactivity of Four Murine Monoclonal Anti–CD22 Antibodies," *Cellular Immunology*, 118:85–99, 1989.

May, R.D. et al., "Selective Killing of Normal and Neoplastic Human B Cells with Anti–CD19–and Anti–CD22–Ricin A Chain Immunotoxins," *Cancer Drug Delivery*, 3(4):261–272, 1986.

Kiesel, S. et al., "Functional Evaluation of CD19–and CD22–Negative Variants of B–Lymphoid Cell Lines," *Immunology*, 64:445–450, 1988.

Raso, Vic, an Griffin, Thomas, "Specific Cytotoxicity of a Human Immunoglobulin–Directed Fab'–Ricin A Chain Conjugate," *The Journal of Immunology*, 125(6):2610–2616, 1980.

Shen, G. et al., "Evaluation of Four CD22 Antibodies As Ricin A Chain–Containing Immunotoxins for The In Vivo Therapy of Human B–Cell Leukemias and Lymphomas," *International Journal of Cancer*, 42:792–797, 1988.

Thorpe, P.E. et al., "Modification of the Carbohydrate in Ricin with Metaperiodate—Cyanoborohydride Mixtures," *European Journal of Biochemistry*, 147:197–206, 1985.

Till, M. et al., "An Assay That Predicts the Ability of Monoclonal Antibodies to Form Potent Ricin A Chain–Containing Immunotoxins," *Cancer Research*, 48:1119–1123, 1988.

Vitetta, E.S. et al., "Redesigning Nature's Poisons to Create Anti–Tumor Reagents," *Science*, 238:1098–1104, 1987.

Vitetta, E.S. et al., "Phase I Immunotoxin Trial in Patients with B–Cell Lymphoma," *Cancer Research*, 51:4052–4058, 1991.

(List continued on next page.)

*Primary Examiner*—Toni R. Scheiner
*Attorney, Agent, or Firm*—Arnold White & Durkee

[57] ABSTRACT

The anti-tumor activity of a mixture of anti-CD22 and anti-CD19 immunotoxins is shown to be significantly enhanced in SCID/Daudi mice with disseminated human Daudi lymphoma. Unexpectedly identical enhancement was observed employing a combination of the anti-CD22 immunotoxin with unconjugated anti-CD19 antibodies. Thus combinations of an anti-CD22 immunotoxin and an anti-CD19 immunotoxin or antibody act synergistically and provide advantageous compositions and methods for immunotherapeutic treatment of various diseases including cancer and autoimmune disorders. Also disclosed is data indicating that certain anti-CD19 antibodies alone inhibit proliferation of CD19-positive cells by inducing cell cycle arrest.

32 Claims, 11 Drawing Sheets

OTHER PUBLICATIONS

Borrebaeck, "Strategy for the production of human monoclonal antibodies using in vitro activated B cells," *Journal of Immunological Methods*, 123:157–165, 1989.

Dörken et al., "HD39 (B3), A B Lineage–Restricted Antigen Whose Cell Surface Expression is Limited to Resting and Activated Human B Lymphocytes," *The Journal of Immunology*, 136(12):4470–4479, 1986.

Ghetie et al., "The Antitumor Activity of an Anti–CD22 Immunotoxin in SCID Mice With Disseminated Daudi Lymphoma Is Enhanced by Either an Anti–CD19 Antibody or an Anti–CD19 Immunotoxin," *Blood*, 80(9):2315–2320, 1992.

Goding, "Antibody Production by Hybridomas," *Journal of Immunological Methods*, 39:285–308, 1980.

Jansen et al., "Establishment of a Human t(4;11) Leukemia in Severe Combined Immunodeficient Mice and Successful Treatment Using Anti–CD19 (B43)–Pokeweed Antiviral Protein Immunotoxin," *Cancer Research*, 52:406–412, 1992.

Mason et al., "Value of Monoclonal Anti–CD22 (p135) Antibodies for the Detection of Normal and Neoplastic B Lymphoid Cells," *Blood*, 69(3):836–840, 1987.

Moldenhauer et al., "Characterization of a Human B Lymphocyte–Specific Antigen Defined by Monoclonal Antibodies HD6 and HD39," *Leukocyte Typing II*, vol. 2, Chapter 7, pp. 97–107. (1986).

Osband and Ross, "Problems in the investigational study and clinical use of cancer immunotherapy," *Immunology Today*, 11(6):193–195, 1990.

Vuist et al., "Poentiation by Interleukin 2 of Burkitt's Lymphoma Therapy with Anti–Pan B (Anti–CD19) Monoclonal Antibodies in a Mouse Xenotransplantation Model," *Cancer Research*, 49:3783–3788, 1989.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:1:

TGGATCCGAC ATGTCAGA                    18

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:2:

CATCCTTGCA GGGCTTCAGT                  20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:3:

CATTATCCAA GCTCCCAAAT                  20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:4:

CATATTTCTC GCTCGTGGTG                  20

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: oligonucleotide ( x i ) SEQUENCE DESCRIPTION: SEQ ID NO:5:

```
CATATTTCCC GCTCGCGTGA                    20
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:6:

```
CCTTGTTCCT CTGGATCTTT                    20
```

EPITOPE-SPECIFIC MONOCLONAL ANTIBODIES AND IMMUNOTOXINS AND USES THEREOF

BACKGROUND OF THE INVENTION

The present application is a continuation-in-part of U.S. patent application Ser. No. 07/899,781, filed Jun. 17, 1992. The entire text and figures of each of U.S. Ser. Nos. 07/899,781, now abandoned and 07/967,072 are specifically incorporated herein by reference without disclaimer.

The government owns rights in the present invention pursuant to NIH grants CA-28149 and CA-41087.

FIELD OF THE INVENTION

The present invention relates generally to immunotherapeutic compositions and methods for controlling cell proliferation. The invention particularly concerns anti-CD19 antibody compositions and methods for their generation and use, including their use as anti-proliferative agents and their use in combination with an anti-CD22 immunotoxin conjugate to achieve enhanced or synergistic killing of B cells.

DESCRIPTION OF THE RELATED ART

B cell tumors account for a significant proportion of human lymphoid tumors, such as non-Hodgkins lymphomas, chronic lymphocytic leukemias (CLL), and prolymphocytic chronic lymphocytic leukemia. The available methods for predicting the clinical course of such diseases and treating these patients are often unsatisfactory. Furthermore, certain human B cell lymphomas have been found to be generally unresponsive to chemotherapy regimens, and the numbers of resulting fatalities is unfortunately high.

Five modalities of therapy have been used during the past 30 years to treat B cell tumors. The modes of therapy include: a) radiation therapy, either total body or local radiation; b) adrenal steroids; c) alkylating agents; d) combination therapy such as chlorambucil and prednisone; and e) splenectomy. Complications due to these modes of tumor treatment are many and often include anorexia, alopecia, severe nausea, ulceration of the intestinal tract, and enhanced susceptibility to infection. Moreover, the deaths related to complications of therapy are significant. For example, 16% of the deaths of patients diagnosed with CLL have been attributed to complications of therapy. Such drawbacks prompted the search for other therapeutic regimens.

The possibility of utilizing the exquisite specificity of antibodies to direct cytotoxic agents to tumor cells has been considered since the studies of Ehrlich (1960). In recent years, the use of conjugates of cell-reactive antibodies and the A chains of toxins such as ricin or diphtheria toxin have been investigated. Such immunotoxin conjugates have been used to kill normal and malignant target cells both in vitro and in vivo. They have been used clinically in the management or treatment of a variety of diseases or disorders, including the treatment of autoimmune diseases, various malignancies, and the purging of T-cells or tumor cells from bone marrow before transplantation (Vitetta et al., 1987).

A number of monoclonal antibodies (MAbs) directed against B cell-restricted antigens, i.e., antigens expressed on normal and neoplastic human B lymphocytes, have been developed and characterized (for a review, see Nadler, 1986). These include antibodies directed against CD19 and CD22. CD19 is a B cell-restricted 95 kD glycoprotein that is expressed early in B cell ontogeny. CD19 is normally lost during the terminal stages of B cell differentiation, but is present on >90% of all B cell tumors (Anderson et al., 1984; Campana et al., 1985; Pezzuto et al., 1986). CD22 is a B cell-restricted glycoprotein, comprising two chains of 130 and 140 kD, which is also expressed on certain B cell tumors (Dörken et al., 1986).

Immunotoxins employing both anti-CD19 and anti-CD22 antibodies have been demonstrated to specifically kill normal and neoplastic human B cells (May et al., 1986). Subsequent analyses demonstrated various ricin A chain-containing anti-CD19 and anti-CD22 immunotoxins to be potentially useful reagents for the clinical treatment of human B cell leukemias and lymphomas (Ghetie et al., 1988a; Shen et al., 1988). The use of modified components in immunotoxin conjugates, such as Fab' antibody fragments and deglycosylated ricin A chain (dgA), has also been investigated.

Development of this technology led to clinical trials using immunotoxins, some of which have generated promising results. For example, in one study, partial tumor remission was observed in certain non-Hodgkin's lymphoma patients treated with anti-CD22 immunotoxins comprising a univalent Fab' antibody fragment coupled to dga (Vitetta et al. 1991). Anti-CD19 coupled to blocked ricin has also been found to exhibit anti-tumor activity following administration to patients with B cell neoplasms (Grossbard et al., 1992).

There is, however, room for improvement in immunotoxin therapy, both in the numbers of patients exhibiting a positive response and in the magnitude of the anti-tumor effects observed. Currently, the administration of immunotoxins is also associated with adverse side effects, including vascular leak syndrome and kidney failure. A further difficulty encountered in this type of immunotherapy is that caused by tumor heterogeneity, i.e. the difficulty in effectively targeting and killing all tumorigenic cells. Also, ricin A chain-containing immunotoxins exhibit a shorter half life in vivo than their unconjugated antibody counterparts, which may be a further factor limiting their clinical effectiveness.

SUMMARY OF THE INVENTION

The present invention addresses one or more of these or other of the disadvantages in the prior art by providing improved methods and compositions for use in immunotherapy. In part, the invention is directed to the use of unconjugated anti-CD19 antibodies to inhibit the proliferation of B cells. The invention also concerns the use of a combination of an anti-CD19 antibody, either as an immunotoxin conjugate or an unconjugated antibody, with an anti-CD22 immunotoxin in various immunotherapeutic treatment strategies. The use of these agents in combination gives rise to an enhanced and surprisingly effective means of specifically deleting B cells.

The invention, in part, embodies the discovery that the anti-tumor activity resulting from the co-administration of an anti-CD22 immunotoxin with certain anti-CD19 immunotoxins is enhanced in vivo to a greater extent than one might have predicted from the effects of either agent alone. A particular advantage provided by this invention is that it addresses the problem of tumor heterogeneity. It is proposed that the use of a combination of agents based upon anti-CD22 and anti-CD19 antibodies provides a means of killing tumor cells which lack one or other of these antigens on their cell surface.

Certain anti-CD19 antibodies and immunotoxins are contemplated to be particularly useful in connection with the present invention. These are antibodies that bind to substantially the same epitope as the antibody termed HD37 (Dörken et al., 1983). As used herein, the term "substantially the same epitope" is used to describe antibodies that are able to compete for the same antigenic region of an antigen. The present disclosure contains preferred methods and techniques for use in determining the extent of competition between antibodies for a distinct epitope. However, alternative techniques are also available as will commonly be known to those of skill in the art of immunochemistry. Examples of suitable antibodies include, for example, the anti-CD19 antibodies termed 4G7 and BU12. The isolation, characterization and sources of antibodies specific for the CD19 antigen have been described in Knapp, et al. (1989), incorporated herein by reference.

The identification of an antibody or antibodies that bind to CD19 at substantially the same epitope as HD37 is a fairly straightforward matter. This is exemplified herein by the determination that both 4G7 and BU12 bind to an epitope overlapping the binding site for HD37, while B43 binds to a distinct, non-overlapping, epitope. Such determinations can be readily determined using any one of variety of immunological screening assays in which antibody competition can be assessed, as is known to those of skill in the art.

In general, competition assays may be any one of a range of immunological assays based upon antibody binding, and the HD37 antibodies would be detected by means of detecting a label, associated with the antibodies, e.g., using streptavidin in the case of biotinylated antibodies or by using a chromogenic substrate in connection with an enzymatic label or by simply detecting a radiolabel. An antibody that binds to the same epitope as HD37 will be able to effectively compete for binding and thus will significantly reduce HD37 binding, as evidenced by a reduction in labelled antibody binding. In the present case, after mixing the labelled HD37 antibodies with the test antibodies, suitable assays to determine the remaining reactivity include, e.g., ELISAs, RIAs or western blots using human B cells; immunoprecipitation of CD19; ELISAs, RIAs or immunofluorescent staining of recombinant cells expressing human CD19; indirect immunofluorescent staining of B cells; reactivity with peripheral blood mononuclear cells or B cell surface determinants by "FACS or indirect immunofluorescence". This latter method may also be employed to show that the epitopes recognized by HD37 are distinct from that of B43.

The reactivity of the labelled HD37 antibodies in the absence of any test antibody is the control high value. The control low value is obtained by incubating the labelled antibodies with unlabelled antibodies of the same type, when competition would occur and reduce binding of the labelled antibodies. A significant reduction in labelled antibody reactivity in the presence of a test antibody is indicative of a test antibody that recognizes the same epitope, i.e., one that "cross-reacts" with the labelled antibody. A "significant reduction" in this aspect of the present application may be defined as a reproducible (i.e., consistently observed) reduction in binding of at least about 15% at a ratio of about 1:100, or more preferably, of between about 5% and about 20% at a ratio of 1:100.

Test antibodies to be examined may be obtained from a variety of sources, such as an anti-CD19 hybridoma. To test the epitope specificity of any given antibody a competition radioimmunoassay (RIA) is preferably employed. In one such embodiment of a competition RIA, one would pre-mix labelled HD37 antibody with varying amounts of the test antibodies prior to applying the mixture to the antigen-coated wells in the RIA plate. Binding interference is detected when the test antibodies bind overlapping epitopes, that is, when the binding of labeled HD37 is reduced by the presence of a test antibody which recognizes the same epitope. In order to measure qualitatively and quantitatively the interference, the two antibodies are mixed in a variety of ratios. The relative ratios are dependent on the binding affinity calculated for each antibody as determined by standard Scatchard plot analysis. In these cases, one would incubate the labelled antibodies with the test antibodies to be examined at various ratios (e.g., 1:1, 1:10 and 1:100, dependent on the relative binding affinities) and, after a suitable period of time, one would then assay the reactivity of the labelled HD37 antibodies and compare this with a control value in which no potentially competing antibody (test) was included in the incubation. This approach is used in Example III of the present disclosure. An example of a less characterized anti-CD19 antibody that may be tested is 8EB1, described by Rigley and Callard (1991).

A further and particularly important aspect of the present invention is the discovery that the action of an anti-CD22 immunotoxin can be potentiated not only by an anti-CD19 immunotoxin, but also by unconjugated anti-CD19 antibodies and anti-CD19 antibodies lacking Fc portions. In contrast, no enhanced effects are observed following administration of an anti-CD19 immunotoxin in combination with an unconjugated anti-CD22 antibody. This development has thus created the opportunity to use an anti-CD22 immunotoxin in combination with an unconjugated anti-CD19 antibody to obtain an increased level of B cell killing without increasing the amount of toxin administered.

Accordingly, in certain embodiments, the present invention provides a method for causing B cell death, by delivering a toxin to a B cell, and a method for potentiating the B cell cytotoxicity of an anti-CD22 immunotoxin. These methods comprise contacting the B cells with an anti-CD22 immunotoxin and an HD37-like anti-CD19 antibody, or fragment thereof, in a combined amount effective to kill B cells.

As used herein, the term "immunotoxin" refers to a conjugate comprising an antibody, or fragment thereof, conjugated to one or more toxin molecules. An anti-CD22 immunotoxin will, naturally, comprise an anti-CD22 antibody or fragment thereof, and an anti-CD19 antibody will comprise an anti-CD19 antibody or fragment thereof. Various anti-CD22 antibodies are contemplated to be of use in accordance with the present invention, including, for example, UV22-1, UV22-2, HD6, and RFB4 (Li et al., 1989, Campana et al., 1985, Dörken et al., 1983, Moldenhauer et al., 1986). In certain embodiments, the use of RFB4 antibodies is preferred because the RFB4-deglycosylated ricin A chain has the highest cytotoxicity of the many anti-CD22-dgAs tested. Alternatively, one may generate a distinct anti-CD22 or HD37-like anti-CD19 antibody using the monoclonal antibody technology which is generally known to those of skill in the art.

It is contemplated that either intact antibodies, such as bivalent IgG molecules, or fragments thereof, may be used in accordance with the present invention. In regard to unconjugated anti-CD19 antibodies, both the use of IgG and F(ab')$_2$ fragments is envisioned. One may wish to employ a univalent antibody fragment, either alone, or as a component of an immunotoxin. Examples of such univalent fragments include, for example, Fab', Fab'Fc, or Fab fragments.

In regard to the toxin components of the immunotoxin, it is contemplated that any one of a variety of toxins may be employed. Included in the term "toxin" are the commonly designated toxins such as poisonous lectins, ricin, abrin, modeccin, botulina and diphtheria toxins, as well as other toxic agents such as radio-isotopes, cytotoxic and carcinostatic drugs. Of course, combinations of the various toxins could also be coupled to one antibody molecule thereby accommodating variable cytotoxicity.

Preferred toxin components for use in the present invention are the A chain portions of the above toxins, with ricin A chain being particularly preferred, and deglycosylated ricin A chain being even more particularly preferred. As used herein, the term "ricin" is intended to refer to ricin prepared from both natural sources and by recombinant means. Various 'recombinant' or 'genetically engineered' forms of the ricin molecule will be known to those of skill in the art. It is contemplated that all such ricin variants or mutants which retain their toxic properties will be of use in accordance with the present invention.

The coupling of one or more toxin molecules to the antibody is envisioned to include many chemical mechanisms, for instance covalent binding, affinity binding, intercalation, coordinate binding, and complexation. The preferred binding is, however, covalent binding.

The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In preferred embodiments, it is contemplated that one may wish to first derivatise the antibody, and then attach the toxin component to the derivatised product. Suitable cross-linking agents for use in this manner include, for example, SPDP (N-succinimidyl-3-(2-pyridyldithio)propionate), and SMPT, 4-succinimidyl-oxycarbonyl-α-methyl-α(2-pyridyldithio)toluene.

Further aspects of the present invention concern methods utilizing anti-CD19 antibodies alone to exert various immunological effects. That is, using anti-CD19 antibodies that are not themselves conjugated to a toxic moiety and that do not require another agent, such as an additional antibody or IT, to achieve their effects. In particular, HD37-like anti-CD19 antibodies are herein shown to exert anti-proliferative activity against CD19$^+$ lymphoma cell lines, such as Daudi, Raji, and Namalwa, and against CD19$^+$ diffuse histiocytic lymphoma cells (DHL-4 cells). These inhibitory effects are manifested by inducing cell cycle arrest, and do not require a toxin or another agent.

In a preferred embodiment the present invention provides a method for inhibiting the proliferation of a CD19$^+$ B cell, comprising: contacting CD19$^+$ B cells with an anti-CD19 antibody that binds to the epitope recognized by the antibody HD37, or a fragment or conjugate thereof, in an amount effective to inhibit the proliferation in said CD19$^+$ B cells. Alternatively the effect of the anti-CD19 on the B cell may be induction of cell cycle arrest. In a more preferred embodiment the anti-CD19 antibody comprises the anti-CD19 antibody HD37, or a fragment or conjugate thereof. Also in a preferred embodiment the anti-CD19 antibody comprises the anti-CD19 antibody BU12, or a fragment or conjugate thereof. In an alternative embodiment the anti-CD19 antibody comprises the anti-CD19 antibody 4G7, or a fragment or conjugate thereof. In a most preferred embodiment the CD19$^+$ B cells are located within an animal and the anti-CD19 antibody, fragment or conjugate is administered to said animal. Of course it is known that these methods may be applicable in a clinical environment, e.g. in the treatment of cancer.

As used herein CD19$^+$ cells are described as those cells having greater that about 1000 CD19 sites per cell as determined by scatchard plot analysis. Alternatively, CD19$^+$ sites per cell may be ascertained indirectly by determining the shift in fluorescent intensity during FACS analysis, as compared to known markers, such as CD45$^+$. Cells containing more than 1000 CD19 sites per cell are defined herein an CD19$^+$ cells, and those cells having less that about 500 sites are referred to as CD19$^-$ cells.

The present invention has direct utility in the clinical treatment of various human diseases and disorders in which B cells play a role. In particular, it provides effective methods and compositions to delete neoplastic B cells, such as in anti-tumor therapy to treat leukemia or non-Hodgkin's lymphoma. Appropriate therapeutic regimens for using the present antibodies or combination of antibodies and immunotoxins will be known to those of skill in the art in light of the present disclosure. For example, methods using a single immunotoxin, such as described by Vitetta et al., *Cancer Res.*, 51:4052, 1991, incorporated herein by reference, may be straightforwardly adapted for use in accordance herewith by substituting the single immunotoxin with the combination of immunotoxins of the present invention.

In certain treatment regimens, it is envisioned that one may administer the combined therapeutic agents of the present invention to a patient essentially at the same time. For such simultaneous co-administration one may either employ a pre-mixed pharmacological composition or "cocktail" of the therapeutic agents, or one may co-administer separate amounts of the anti-CD22 immunotoxin and the anti-CD19 agent from distinct pharmacological formulations. Alternatively, it is contemplated that the two agents may be administered at different times, and yet still result in an advantageous effect, due to their combined physiological actions. Naturally, in the latter case, the immunotherapeutic agents would have been stored separately prior to use. It is contemplated that the combined therapeutic agents of the present invention may be administered to patients in a dose of between about 0.5 and 2 mg/kg.

The methods and compositions of the present invention are also contemplated to be of use in further clinical embodiments such as, for example, in the deletion of B cells which produce undesirable antibodies, as in autoimmune disorders or during xenograft or transplantation processes. In such treatment regimens, a sufficient amount of the combination of therapeutic agents, or HD37-like anti-CD19 antibodies alone, would be administered to the patient to diminish antibody formation. It is contemplated that doses of between about 0.5 and 2 mg/kg would be useful in this regard.

In addition to its clear utility in human treatment regimens, the immunotoxin combination of the present invention will be of use in a variety of other embodiments. In that the anti-CD19 antibodies induce cell cycle arrest, and the combined anti-CD22 immunotoxin and anti-CD19 antibody or immunotoxin result in enhanced B cell killing, it is anticipated that such compositions may be advantageously used in many immunological methods. For example, to inhibit or delete B cells from a population of cells in vitro, allowing one to obtain a population of cells relatively enriched in other components, such as, by way of example, enriched in T cells.

Furthermore, HD37-like antibodies may be employed to induce cell cycle arrest, and hence inhibit proliferation, of CD19-positive cells either in vitro or in vivo. Further embodiments of the present invention concern pharmacological compositions comprising a therapeutically effective combination of an anti-CD22 immunotoxin and an HD37-like anti-CD19 antibody, fragment thereof, or immunotoxin. Preferably, the anti-CD22 immunotoxin of the composition will comprise the antibody RFB4, or a fragment thereof, and the anti-CD19 antibody will be HD37, 4G7 or BU12, or a fragment thereof. The preferred toxin component of the immunotoxin is contemplated to be ricin A chain, with deglycosylated ricin A chain being even more preferred.

Kits for use in the delivery of a toxin to a B cell constitute another embodiment of the invention. The kits of the present invention will typically include a means for containing an anti-CD22 immunotoxin and an HD37-like anti-CD19 antibody, fragment thereof, or immunotoxin in close confinement. The container means will generally include a vial into which the above agents may be placed, and preferably suitably aliquoted. Such container means may include injection or blow-molded plastic containers into which the desired vials are retained. Kits prepared in accordance with the present invention may comprise a single container means in which a mixture or "cocktail" of the agents are stored together. Alternatively, the kit may comprise distinct container means, for example two separate container means each one of which contains an individual therapeutic agent, which may later be used as a combination in accordance herewith.

The kits of the invention may be employed to deliver a toxin to a B cell either in vivo, in any one of the treatment protocols described herein, or in vitro. In the former case, one would naturally employ formulations of the therapeutic agents in a pharmacologically-acceptable vehicle. However, for use in vitro, for example, as a kit for preparing a cell population from which B cells have been depleted, the anti-CD22 and anti-CD19 compounds may be prepared in any one of a variety of forms, such as in a buffered solution.

Still further aspects of the present invention relate to the use of a combination of an anti-CD22 immunotoxin and an HD37-like anti-CD19 antibody, fragment thereof, or immunotoxin, in autologous bone marrow rescue protocols. In such embodiments, one would obtain cells from the bone marrow of an animal, particularly a human patient, and treat such cells ex vivo with the immunotherapeutic agents of the invention in a combined amount effective to kill B cells. One would then administer the treated bone marrow cells to the patient to reconstitute the hemopoietic system.

BRIEF DESCRIPTION OF THE DRAWINGS

FIG. 6 contains three individual panels which are all part of the figure.

DETAILED DESCRIPTION OF THE PREFERRED EMBODIMENTS

Figure 1:
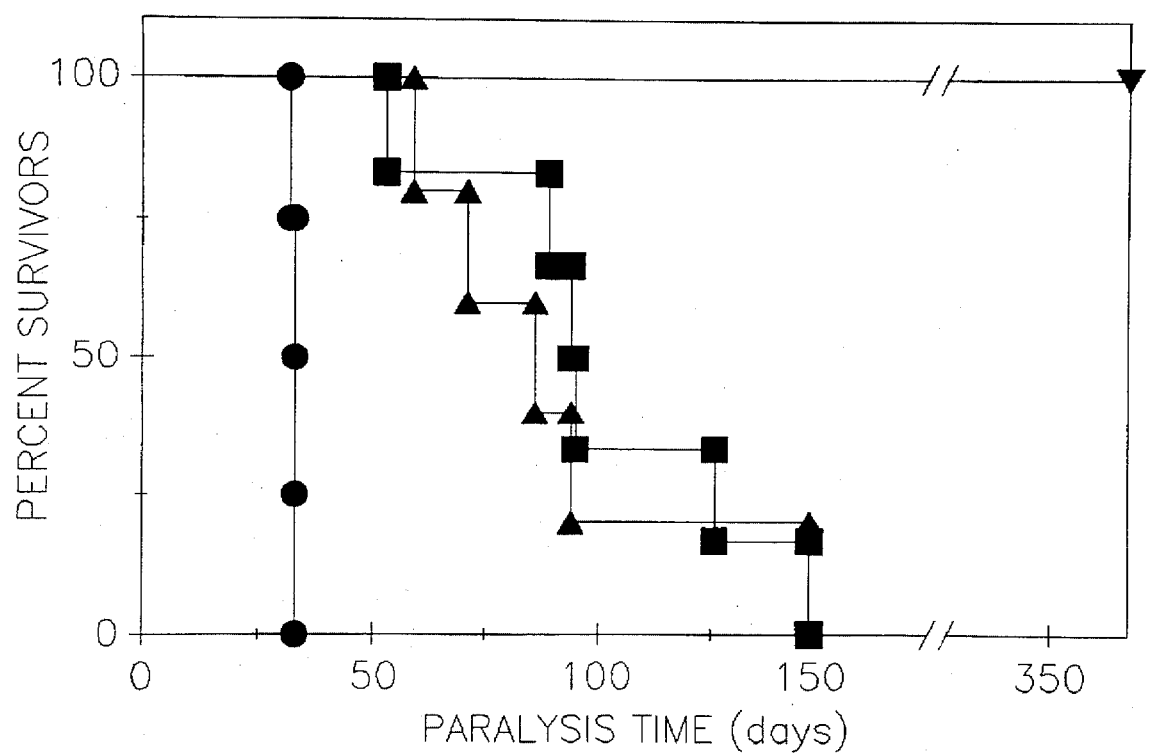
FIG. 1. F(ab')$_2$ fragments of HD37 plus RFB4-dgA induce complete inhibition of tumor growth in SCID/Daudi mice. SCID mice were inoculated i.v. with Daudi cells ($5 \times 10^6$ cells/mouse) and were treated with 4 equal doses as follows: —●— PBS (control) (4 mice); —△— RFB4-dgA (20% LD$_{50}$ dose, totalling 60 µg); —■— RFB4-dgA (20% LD$_{50}$, totalling 60 µg)+HD37-F(ab')$_2$ (equivalent to 20% LD$_{50}$ dose, totalling 50 µg); —▼— RFB4-dgA (20% LD$_{50}$ dose, totalling 60 µg)+HD37-F(ab')$_2$ (equivalent to 200% LD$_{50}$, totalling 500 µg). The percent of survivors was plotted against the paralysis time.

An immunotoxin is a conjugate comprising an antibody directed against a specific cell surface molecule which has been coupled to one or more toxin molecules. Immunotoxins therefore act to deliver toxic agents to specific target cells. Such antibody-toxin conjugates combine the determinant specificity of antibody with the lethal effects of toxic agents thereby providing site-specific immunotherapeutic agents.

In recent years immunotoxins have been used in various animal and clinical trials, including the treatment of patients with B cell tumors. A frequently-used toxin for use in immunotoxins is ricin A chain. However, ricin A chain-containing conjugates have been reported to exhibit a shorter half life in vivo than their unconjugated antibody counterparts, which may reduce their clinical effectiveness. Further factors which may limit the potency of an immunotoxin include the cell surface antigen and particular epitope to which the antibody is directed, the density of the antigen, the antibody affinity, and the pathway of internalization.

Although immunotoxins have been used in clinical trials with some success, both the numbers of patients responding positively and the degree of the resultant anti-tumor effects have often been minimal (Byers & Baldwin, 1988). Occasional and transient tumor reductions have been in patients with melanoma (Oratz et al., 1990; Spitler et al., 1987), breast cancer (Weiner et al., 1989), colon cancer (Byers et al., 1989), and chronic lymphocytic leukemia (Hertler et al., 1988). However, more encouraging results have recently been reported on treating B cell lymphoma patients with an immunotoxin containing deglycosylated ricin A chain (Vitetta et al., 1991). The antibody portion of the immunotoxin used in this study was directed against a B cell marker termed CD22.

A further limitation in immunotoxin therapy for the treatment of any type of cancer is that of tumor heterogeneity, i.e. the difficulty in effectively targeting and killing all tumorigenic cells. Regarding the treatment of B cell tumors in this light, the present inventors noted that certain B cell-specific antigens are expressed on a wider range of tumors than CD22. For example, an anti-CD19 antibody, HD37, recognizes 50–100% of tumor cells from over 90% of B lymphomas, whilst the anti-CD22 antibody, RFB4, reacts with only 15–100% of tumor cells in 60–70% of patients with B cell lymphoma.

CD19 is a membrane receptor involved in signal transduction in B lymphocytes (Uckun et al., 1988; Kozmik et al., 1992) and it appears on normal B cells early in ontogeny (Campana et al., 1985; Pezzutto et al., 1986). CD19 belongs to a membrane protein complex on B lymphocytes, containing CD19, CR2 (or CD21, a receptor for complement), TAPA-1 (a target for anti-proliferation antibody), Leu-13 (Matsumoto et al., 1993; Bradbury et al., 1992) and other unidentified proteins. The signal-transducing function of CD19-CR2 complex potentiates the response of B cells to antigen in vivo (Hebell et al., 1991).

B cells appear to have two signal transduction complexes, associated with membrane IgM and CD19, that activate phospholipase C (PLC) by different mechanisms and that can interact synergistically to enhance this function by the CD19 pathway (Carter et al., 1991). Anti-CD19 also stimulate in vitro colony formation in ALL cells (Ledbetter et al., 1988). TAPA-1 and Leu-13 increase the complexity and versatility of signaling through this multimolecular structure. MAb directed against CD19, CD21, TAPA-1, and Leu-13 can induce anti-proliferation effects in B cells (Bradbury et al., 1992). In contrast, anti-CD19 Abs strongly inhibit proliferation of resting mature B cells in response to stimulation with anti-IgM Abs (Pezzutto et al., 1987) and block the in vitro differentiation of mature B cells into plasma cells (DeRie et al., 1989; Golay et al., 1987). Hence, CD19 [like membrane Ig; Bzixeras et al., 1993] can mediate both positive and negative signals (Callard et al., 1992) depending on the differentiative stage of the normal B-cell and the type of signal involved i.e. proliferation vs. differentiation (Ledbetter et al., 1988).

In in vitro studies, the inventors found the anti-CD19 immunotoxin, HD37-dgA, to be 10-fold less potent than the anti-CD22 immunotoxin RFB4-dgA (Ghetie et al., 1988a; Shen et al., 1988). However, as the levels of CD19-positive B cells would be expected to be higher in a given patient and the CD19 expression more homogenous, the inventors reasoned that the actions of anti-CD19 immunotoxins in vivo warranted investigation.

To study the in vivo effects of these immunotoxins, the inventors employed their SCID/Daudi mouse model of disseminated human B lymphoma for preclinical evaluation. SCID mice inoculated intravenously with $CD19^+$ $CD22^+$ Burkitt's lymphoma cells (Daudi) have been shown to develop extranodal disease in ovaries, kidneys, and bone marrow and to exhibit hind legs paralysis prior to death (Ghetie et al., 1990; 1991). This model has previously been used to analyze the anti-CD22 Fab'-dga immunotoxin conjugates subsequently developed for phase I/II clinical trials in patients with refractory non-Hodgkin lymphoma (NHL).

SCID/Daudi mice were treated with the two immunotoxins, or their unconjugated antibodies, in different combinations (cocktails) to determine whether certain cocktails exhibited enhanced anti-tumor activity. Unexpectedly, it was found that a combination of anti-CD22 and anti-CD19 immunotoxins acted synergistically and enhanced anti-tumor activity as compared to that of either agent alone.

Even more surprisingly, the anti-tumor activity of the anti-CD22 immunotoxin was equally enhanced in combination with unconjugated anti-CD19 antibodies. In contrast, enhancement was not observed when mice were injected with a mixture of anti-CD19 immunotoxins and anti-CD22 unconjugated antibodies. The advantageous effects of the anti-CD19 antibodies in combination with anti-CD22 ITs proved to prolong the survival of SCID/Daudi mice to one year—at which time they still remained tumor-free.

Certain aspects of the present invention are therefore based upon these surprising discoveries, namely that the tumoricidal action of an anti-CD22 immunotoxin conjugate is synergistic with the actions of an anti-CD19 immunotoxin or unconjugated antibody. The use of a combination of these agents results in co-operative anti-tumor activity. Their combined use thus provides a surprisingly effective means of specifically deleting B cells and represents a distinct advantage over current immunotherapeutic treatment strategies.

Other aspects of the present invention concern the actions of anti-CD19 antibodies alone. The synergistic activity described above prompted the inventors to further study the role of anti-CD19 Abs on tumor cell growth in vitro and to determine whether CD19 would negatively signal tumor cells in vitro and in vivo.

The anti-CD19 antibody HD37 was found to have antiproliferative activity ($IC_{50}=5.2-9.8\times10^{-7}M$) on three CD19$^+$ Burkitt's lymphoma cell lines (Daudi, Raji, and Namalwa) but not on a weakly CD19-positive (CD19$^{lo}$) pre-B cell tumor (Nalm-6). The inhibitory effect was manifested by cell cycle arrest, but not apoptosis. Results using three additional anti-CD19 Abs, indicate that the affinity of the antibody and the epitope which it recognizes likely effect its capacity to transmit a signal that induces cell cycle arrest. Hence, it is proposed that Abs can exert anti-tumor activity by a variety of mechanisms which may be exploited in clinical treatment.

The combinations of immunotoxins disclosed herein, and cell cycle arrest-inducing anti-CD19 antibodies in accordance with the invention, are proposed to be of use in the clinical treatment of various human diseases and disorders in which B cells play a role. In particular, they may be used in anti-tumor therapy to treat, for example, patients with leukemia or non-Hodgkin's lymphoma. Methods of immunotoxin treatment using a single immunotoxin have been described in the art, for example, see Vitetta et al., *Cancer Res.*, 51:4052, 1991, incorporated herein by reference. It is contemplated that such methods may be adapted for use in accordance with the present invention by substituting the single immunotoxin of the prior art for the advantageous combination, or the anti-CD19 component, disclosed herein.

It is contemplated that the combination of immunotoxins or anti-CD19 antibodies could be formulated together with any of the pharmaceutical compositions currently known in the art in preparation for human administration. Any pharmaceutically acceptable carrier may be used, and particularly those designed for parenteral administration, such as administration via an intravenous route. The precise compositions and use of such pharmaceutical carriers will be known to those of skill in the art in light of the present disclosure.

The advantageous immunotoxin combination or anti-CD19 treatment of the present invention may also be used in conjunction with other anti-cancer therapies, Including, for example, radiotherapy, chemotherapy, or with the administration of other therapeutic agents, such as interleukins, antibodies to interleukins or soluble interleukin receptors. In addition to use in direct infusion therapy, it is contemplated that the immunotoxins may also be used to delete tumor cells in ex vivo treatment protocols, such as in bone marrow purging. Treated bone marrow cells could then be re-administered to the patient as part of ongoing tumor therapy.

The methods and compositions of the present invention are also contemplated to be of use in various treatment regimens other than in anti-cancer strategies. They may be used in any clinical situation where the deletion of B cells would be an advantage to the patient. For example, in the deletion of B cells which produce undesirable antibodies, as in autoimmune disorders such as diabetes or arthritis, or during or during graft or transplant processes. In such treatment regimens, a sufficient amount of the combination of therapeutic immunotoxins or anti-CD19 antibodies would be administered to the patient to diminish antibody formation and yet not to destroy all the B cells.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Generation of Antibodies and Immunotoxins

1. Antibodies

Mouse IgG$_1$ monoclonal antibodies specific for CD22 (RFB4) or for CD19 (HD37) and the purified isotype-matched (IgG$_1$) myeloma protein (MOPC-21) (control) were used. Both RFB4 and HD37 were prepared by Abbott Biotech (Needham Heights, Mass.). The MOPC-21 myeloma protein was obtained from Cappel (West Chester, Pa.).

The RFB4 hybridoma cell line may be raised as described by Campana et al., *J. Immunol.*, 134:1524, 1985, incorporated herein by reference, and the HD37 hybridoma cell line may be raised as described by Dörken et al., *Verh. Dtsch. Ges. Path.*, 67:65, 1983, incorporated herein by reference. Antibodies may be prepared from ascitic fluid or culture medium by ammonium sulfate precipitation (final concentration 45%). The precipitates can be dissolved and dialyzed against an appropriate buffer and further purified by chromatography, for example, using hydroxylapatite and phosphate buffer pH 7.2; SP-SEPHADEX (gel filtration matrix) and citrate buffer pH 4.0; or Staphylococcal Protein A-SEPHAROSE (gel filtration matrix) and borate buffer, pH 9.0.

2. F(ab')₂ Fragments of HD37

F(ab')₂ was obtained by digesting HD37 with pepsin as described in (Ghetie et al., 1988b). Briefly, pepsin was added to the antibody solution, in 0.1M citrate buffer pH 3.7, at a level of 20 mg pepsin/g IgG. The digestion was allowed to proceed at 37° C. for 2–8 hours with occasional stirring (2 hours for HD37, and 8 hours for RFB-4). The pH of the digest was then brought to approximately 8.0 with 1M sodium hydroxide. The digest was applied to a SEPHACRYL (gel filtration matrix) S-200HR column equilibrated in 0.1M phosphate buffer with 0.003M Na₂EDTA (PBE) and the F(ab')₂ peak was collected and concentrated by CH2 spiral cartridge concentrator Y30 (Amicon, Denvers, Mass.) at 4° C. The F(ab')₂ fragments were purified by gel permeation HPLC using a preparative 21.5×600 mm TSK 3000SWG column (ULTROPAC (HPLC column), LKB).

3. Immunotoxins

Deglycosylated ricin A chain was prepared as described in (Thorpe et al., 1985) and was purchased from Inland Biologicals (Austin, Tex.).

HD37-dgA, RFB4-dgA and MOPC-21-dgA were prepared as described previously (Ghetie et al., 1988a, Knowles & Thorpe, 1987), but using SMPT as the derivatizing agent. SMPT was added to a solution of F(ab')₂ (10 mg/ml) in 0.1M phosphate buffer, 0.003M Na₂EDTA, pH 7.5 (PBE), to give a final concentration of 1 mM. After 30 minutes at room temperature, the solution was filtered on a column of SEPHADEX G-25 (gel filtration matrix) (30×2 cm) equilibrated with PBE. The derivatized protein was then mixed with reduced A chain (dissolved in PBE) using 1.3 mg A chain/mg F(ab')₂, concentrated by ultrafiltration to 2–3 mg/ml, and maintained for 2 hours at 25° C. and overnight at 4° C. The mixture was purified according to Knowles & Thorpe (1987).

The purity of the immunotoxins was determined by sodium dodecyl sulphate-polyacrylamide electrophoresis (SDS/PAGE) under nonreducing and reducing conditions on 7.0% gels (Laemmli, 1970) and by gel permeation high performance liquid chromatography on an analytical 7.5×600 mm TSK 3000SW column (SPHEROGEL) (HPLC column) (Pharmacia).

EXAMPLE II

Combination Therapy

A. Materials and Methods

1. Cells

The in vitro adapted surface IgM+ Burkitt's lymphoma cell line, Daudi, was maintained by serial passages in RPMI 1640 medium containing 10% heat-inactivated fetal bovine serum, 100 units/ml penicillin, 100 µg/ml streptomycin, and 100 mM L-glutamine (complete medium). The cells were grown in a humidified atmosphere of 5% $CO_2$ and air. Cells were washed with sterile PBS, and the cell suspension was adjusted to an appropriate concentration for inoculation ($5\times10^7$/ml). Viability of the cell was determined by Trypan blue exclusion.

2. Animals

The female SCID mice (C.B-17 SCID/SCID) were obtained from our colony at the University of Texas. They were housed and maintained in modified barrier facilities by the Animal Resources Center, in microisolator cages under sterile conditions. Animals were given autoclaved food and sterile water ad libitum, and all manipulations were performed in a laminar flow hood.

3. SCID/Daudi Mice

Six- to 10-week-old SCID mice were given injections in the tail vein, of $5\times10^6$ Daudi cells in 0.1 ml PBS solution. Mice were followed daily and were sacrificed either by the onset of paralysis or when were in a critical condition.

4. Cytotoxicity Assay

The cytotoxic activity of the immunotoxins was determined using Daudi cells in a [³H]-leucine incorporation assay, as described in (Ghetie et al., 1988a). Briefly, cells in RPMI Medium 1640 containing 10% FCS, glutamine, and antibiotics were distributed into triplicate wells (96-well microtiter plates) containing medium and a range of immunotoxin concentrations and incubated for 24–48 h at 37° C. The cells were centrifuged and washed twice in leucine-free RPMI 1640 containing 10% FCS and were resuspended in the same medium. Cells were pulsed for 4 hours at 37° C. in 5% $CO_2$ $_{with}$ 5 µCi [³H]leucine (Amersham, Arlington, Va.). Wells were harvested on a TITERTEK™ dell harvester (Flow Labs, Rockville, Md.) and the radioactivity on the filters was counted in a liquid scintillation spectrometer. The reduction in [³H]-leucine incorporation in cells cultured with the immunotoxins, as compared to untreated controls, was used to assess killing (Krolick et al., 1980).

5. Cell-Free Rabbit Reticulocyte Assay

A modification of the procedure described by Press et al. (1988) was used to determine the activity of the dgA portion of the immunotoxins used for therapy.

6. Determination of the $LD_{50}$ of the Immunotoxins in Mice

The $LD_{50}$ of all three immunotoxins in 20 g BALB/c or SCID mice was determined as described previously (Ghetie et al., 1991; Fulton et al., 1988). Groups of 4 normal mice were (8–10 weeks old were given i.p. injections of 0.2, 0.4, or 0.6 mg of immunotoxin. The mice were weighed prior to injection and daily thereafter and were observed for 7 days. The $LD_{50}$ values were determined by plotting the percentage mortality versus the injected dose.

7. Immunotoxin and Cocktail Therapy

Scid mice were inoculated with Daudi cells 24 hours prior to treatment with immunotoxins or antibodies. Groups of 5–7 mice were injected retroorbitally with a total of 20 or 40% of the $LD_{50}$ dose of each immunotoxin in a single course of four equal doses on days 1, 2, 3 and 4 after tumor inoculation. Other mice were injected with antibody alone in amounts equivalent to that used in the respective immunotoxin or were injected with the following cocktails:

(a) RFB4-dgA (20% $LD_{50}$)+HD37-dgA (20% $LD_{50}$);
(b) RFB4-dgA (20% $LD_{50}$)+20% $LD_{50}$ equivalent amounts of antibodies RFB4, HD37 or MOPC-21;
(c) HD37-dgA (20% $LD_{50}$)+20% $LD_{50}$ equivalent amounts of antibodies HD37, RFB4 or MOPC-21;
(d) MOPC-21-dga (20% $LD_{50}$)+20% $LD_{50}$ equivalent amounts of antibodies MOPC-21 or RFB4.

Three groups of mice were treated with HD37 antibody (40% $LD_{50}$ equivalent) at different stages of tumor growth. Two other groups of 5 mice were treated with either HD37 antibody or with its F(ab')₂ fragment.

Mice were observed daily for the onset of posteriors paresis or paralysis. At the end point, which is either the onset of paralysis of hind legs or when the mice were in a critical condition, the mice were euthanized with ether and gross and microscopic examinations were performed and the major organs, i.e. ovaries, kidneys, spleen, liver, lungs and heart. Excised tissues were fixed in 10% buffered formalin, embedded in paraffin, sectioned, and stained with hematoxylin-eosin. Since in the case of treatment with cocktails the paralysis was a rather rare event, mice were sacrificed when they exhibited signs of illness.

B. Results

1. Characterization of Immunotoxins

The HD37-dgA and RFB4-dgA immunotoxins used in these studies are described in Table 1. The data show that they differ only in their ability to kill Daudi cells in vitro. Thus, HD37-dgA is 10-fold less cytotoxic to Daudi cells than RFB4-dgA, as judged by their $IC_{50}$'s.

TABLE 1

CHARACTERIZATION OF IMMUNOTOXINS USED IN SCID/DAUDI MICE

| Assay | dgA-Immunotoxin | |
|---|---|---|
|  | HD37 | RFB4 |
| SDS-PAGE/HPLC on TSK3000 (% of major peak) | 69 | 70 |
|  | 45 | ND |
| T½ of dissociation in vitro (hrs) | 33.5 | 37.8 |
| T½β in mice (hrs) | 80[a] | 97[b] |
| Antibody activity (% of initial) | 7.8 | 8.0 |
| dgA activity in reticulocyte assay ($IC_{50}$, $M \times 10^{-12}$) | 4.5 | 0.5 |
|  | 16 | 12 |
| Daudi killing assay ($IC_{50}$, $M \times 10^{-11}$) | 0.5 | 0.5 |
| $LD_{50}$ (mg/kg) |  |  |
| Endotoxin by LAL-assay (EU/mg) |  |  |

[a]$Ka = 3.6 \pm 0.4 \times 10^8 M^{-1}$[8]
[b]$Ka = 9.1 \pm 1.8 \times 10^8 M^{-1}$[9]

2. Effects of Immunotoxins and Antibodies on the Mean Paralysis Time (MPT)

The MPT represents an accurate measurement of the anti-tumor activity of immunotoxins in the SCID/Daudi model (Ghetie et al., 1990; 1991). From the dose-dependent curve of mean paralysis time (MPT) the number of tumor cells that are killed in vivo after treatment with immunotoxins can be estimated if it is assumed that the only direct effect of the therapeutic agent is rapid cell killing. The MPT and the estimated number of cells killed by the three immunotoxins and their corresponding antibodies at two different doses (20% and 40% of the $LD_{50}$) is summarized in Table 2. MOPC-21 and MOPC-21-dgA were used as negative controls for the antibodies and immunotoxins.

TABLE 2

THE EFFECT OF DIFFERENT DOSES OF IMMUNOTOXINS OR ANTIBODIES ON THE SURVIVAL OF MICE AND THE EXTRAPOLATED KILLING OF TUMOR CELLS IN VIVO

| Treatment[a] | Dose (% of $LD_{50}$ or its equivalent in mg of antibody) | MPT ± S.D. (days) | Killing of Daudi Cells (%)[b] | Logs |
|---|---|---|---|---|
| PBS | — | 30.6 ± 2.3 (5) | 0 | 0 |
| MOPC-21-dgA | 40 | 29.4 ± 3.3 (5) | 0 | 0 |
|  | 20 | 28.9 ± 3.5 (5) | 0 | 0 |
| MOPC-21 | 40 | 26.0 ± 1.7 (5) | 0 | 0 |
|  | 20 | 29.0 ± 2.8 (5) | 0 | 0 |
| RFB4-dgA | 40[c] | 73.2 ± 7.3 (5) | 99.99 | 4 |
|  | 20 | 50.0 ± 7.0 (5) | 99.10 | 2 |
| RFB4 | 40[c] | 46.2 ± 7.3 (5) | 95.83 | 1 |
|  | 20 | 38.4 ± 5.6 (5) | 85 | <1 |
| HD37-dgA | 40 | 54.9 ± 9.9 (8) | 99.60 | 2 |
|  | 20 | 53.8 ± 8.5 (5) | 99.45 | 2 |
| HD37 | 40 | 57.8 ± 6.1 (8) | 99.88 | 2–3 |
|  | 20 | 43.6 ± 3.7 (5) | 95 | 1 |

[a]SCID mice were inoculated with $5 \times 10^6$ Daudi cells and treated either with immunotoxins (40% or 20% of the $LD_{50}$ dose) or with equivalent amounts of the antibodies indicated on days 1–4 after tumor inoculation. Numbers in parentheses represent the number of mice per group. Statistical significances are as follows:
RFB4-dgA (either 40% or 20% of $LD_{50}$) vs PBS: $p \leq 0.001$
RFB4 (40%) vs PBS: $p < 0.01$ and RFB4 (20%) vs PBS: $p \leq 0.05$
HD37-dgA (either 40% or 20% of $LD_{50}$) vs PBS: $p \leq 0.001$
HD37 (40%) vs PBS: $p < 0.001$ and HD37 (20%) Vs PBS: $p \leq 0.05$
RFB4-dgA (40%) vs HD37-dgA (40%): $p \leq 0.001$
RFB4-dgA (20%) vs HD37-dgA (20%): $p > 0.05$
HD37 (40%) vs RFB4 (40%): $p < 0.001$
HD37 (20%) vs RFB4 (20%): $p > 0.05$
[b]Extrapolated from the paralysis dose response curve; Ghetie et al., 1990
[c]Data from Ghetie et al., 1991

These studies demonstrate that at a 40% $LD_{50}$ dose of either the RFB4-dgA or the HD37-dgA, the MPT is extended as compared with either PBS or with MOPC-21-dgA ($p \leq 0.001$). Treatment with a 40% $LD_{50}$ dose of RFB4-dgA killed 99.99% (4 logs) of Daudi cells, whereas a similar dose of the HD37-dga killed 99.45% (2 logs) of tumor cells. HD37-dgA was less effective than RFB4-dgA as demonstrated by the statistically significant difference between the MPTs of the treated mice (73.2 vs 54.9 days; $p \leq 0.001$). The lower potency of the HD37-dgA is consistent with its inferior in vitro activity (Table 1). The effect of the two immunotoxins became comparable at 20% of the $LD_{50}$ dose as shown by the MPTs of the treated mice (50.0 vs 53.8 days; $p > 0.05$). Furthermore, when administered at either 40% or 20% of the $LD_{50}$ dose, the anti-tumor activity of RFB4-dgA was dose-dependent while that of the HD37-dgA was not. Thus, the MPT of mice injected with RFB4-dgA at 40% of the $LD_{50}$ dose was significantly higher than that at 20% of the $LD_{50}$ dose (73.2 vs 50.0 days; $p \leq 0.001$), whereas the effects of HD37-dgA at both 20% and 40% of the $LD_{50}$ dose were the same (54.9 vs 53.8 days; $p > 0.05$).

The two antibodies, RFB4 and HD37 had modest but statistically significant anti-tumor activities of their own corresponding to 1–2 logs of tumor cell killing. An irrelevant isotype-matched antibody (MOPC-21) had no effect at either dose. The HD37 antibody was more effective than the RFB4 antibody at both doses (MPTs of 57.8 vs 46.2 days, $p \leq 0.001$; 43.6 vs 38.4 days, $p \leq 0.05$). Hence, when the anti-tumor activities of the two immunotoxins is compared with those of their corresponding antibodies, the MPT of mice injected with RFB4-dgA as compared to RFB4 was significantly longer at both doses. In contrast, HD37-dgA and HD37 showed identical anti-tumor activities at 40% of the $LD_{50}$ dose and modest differences at 20% of the $LD_{50}$ dose (or its equivalent in mgs for antibody).

3. Further Characterization of the Anti-Tumor Action of HD37

Since the HD37 antibody was as effective as its immunotoxin in extending the MPT of SCID/Daudi mice, the ability of this antibody to prolong survival when administered at later stages of tumor growth was investigated. The anti-tumor effect of HD37 was achieved only by injecting the antibody at a dose equivalent to that contained in 40% of the $LD_{50}$ dose of the immunotoxin early after tumor inoculation, days 1–4, (Table 3).

TABLE 3

ANTI-TUMOR ACTIVITY OF HD37 ANTIBODY
DURING DIFFERENT STAGES OF TUMOR GROWTH

| Treatment[a] | Treatment regimen | MPT ± S.D. (days) |
|---|---|---|
| MOPC-21 | Days 1–4 | 26.0 ± 1.7 (5) |
| HD37 | Days 1–4 | 52.4 ± 2.6 (5) |
|  | Days 10–13 | 32.0 ± 4.2 (5) |
|  | Days 21–24 | 32.8 ± 4.1 (5) |

[a]SCID mice were treated with a dose of antibody equivalent to that present in 40% $LD_{50}$ dose of the immunotoxin. A single course of treatment was given in 4 equal doses. Numbers in parentheses represent the number of mice in each group. The difference between HD37 (days 1–4) and MOPC-21 is significant ($p \leq 0.001$); but the others are not ($p > 0.05$).

Next, to determine whether treatment with HD37 was dependent on its Fc fragment, the anti-tumor activity of intact antibody was compared with that of its $F(ab')_2$ fragment. Both the $F(ab')_2$ and IgG were found to have equivalent anti-tumor activities when administered as four equal injections (Table 4), even though the former would be predicted to have a 8-fold shorter half life in vivo (Spiegelberg et al., 1965).

TABLE 4

EFFECT OF TREATMENT WITH IgG OR $F(ab')_2$
FRAGMENTS OF HD37 ANTIBODY ON
THE MPT OF SCID/DAUDI MICE

| Treatment[a] | MPT ± S.D. (days) |
|---|---|
| PBS | 30.6 ± 2.3 (5) |
| HD37 IgG | 50.4 ± 6.8 (5) |
| HD37 $(Fab')_2$ | 39.2 ± 6.1 (5) |

[a]SCID mice were injected with 100 μg/mouse of either IgG or $F(ab')_2$ (given in 4 equal doses) on days 1–4 after tumor inoculation. Numbers in parentheses represent the number of mice per group. Statistical significances are as follows:
IgG vs PBS: $p \leq 0.001$
$F(ab')_2$ vs PBS: $p \leq 0.05$
IgG vs $F(ab')_2$: $p \leq 0.05$

4. Effects of Combination Therapy

It was next determined whether the two immunotoxins had a cooperative anti-tumor effect when administered together. The administration of combinations of immunotoxins or immunotoxins and antibody was found to extend the MPT (Table 5). For example, a mixture of a 20% $LD_{50}$ dose of RFB4-dgA and a 20% $LD_{50}$ dose of HD37-dgA showed cooperative anti-tumor activity, resulting in an MPT significantly longer (103.1 days) than that obtained with either individual immunotoxin at either a total of 20% of the $LD_{50}$ dose (50.0 or 53.8 days, $p \leq 0.0001$) or at 40% of the $LD_{50}$ dose (73.2 or 54.9 days, $p \leq 0.0001$) (Tables 2 and 5). The cocktail therefore prolonged survival in a manner consistent with the killing of >5 logs of tumor cells as compared to 2–4 logs for a 20%–40% $LD_{50}$ dose of RFB4-dgA or, 2 logs for either a 40% or 20% $LD_{50}$ dose of HD37-dgA.

Unexpectedly, enhanced anti-tumor activity was also observed when RFB4-dgA was administered with HD37 antibody instead of HD37-dgA. In contrast, when a mixture of RFB4-dgA and RFB4 antibody was injected, the MPT of the immunotoxin was decreased (37.0 vs. 50.0 days) and was even shorter than that observed using the combination of RFB4-dgA and MOPC-21 antibody (51.5 days) or RFB4 antibody alone (46.2 days). This indicates that the RFB4 antibody exerted an expected inhibitory effect on the anti-tumor activity of its immunotoxin, probably by competing for binding sites on the tumor cells.

In contrast, the anti-tumor activity of HD37-dgA was not decreased when it was administered with HD37 antibody (53.8 vs. 50.2 days), suggesting that the anti-tumor activity of HD37-dgA is not due to its toxin moiety, i.e., the antibody and the immunotoxin had similar anti-tumor activity and there was no competition or cooperativity between the two agents in vivo. Importantly, HD37-dgA given in combination with RFB4 or MOPC-21 had the same anti-tumor activity as HD37-dgA alone, indicating that the anti-tumor activity of the anti-CD19 immunotoxin was not potentiated by anti-CD22 antibodies (RFB4).

Hence, unpredictably, administration of a particular combination of an immunotoxin specific to one B cell antigen (CD22) and an unconjugated antibody directed against a second B cell antigen (CD19) has resulted in a major enhancement of tumor cell killing. This is not a general phenomenon since the converse combination did not have this effect.

TABLE 5

EFFECT OF TREATMENT WITH COMBINATIONS OF
IMMUNOTOXINS AND ANTIBODIES ON THE MPT AND THE
EXTRAPOLATED KILLING OF TUMOR CELLS

| Combination Therapy[a] | MPT ± S.D. (days)[b] | Killing of Daudi Logs[c] |
|---|---|---|
| RFB4-dgA + HD37-dgA | 103.1 ± 17.0 (11)[d] | >5[e] |
| RFB4-dgA + HD37 | 100.8 ± 25.2 (11) | >5 |
| RFB4-dgA + RFB4 | 37.0 ± 2.1 (5) | <1 |
| RFB4-dgA + MOPC-21 | 51.5 ± 7.2 (6) | 2 |
| HD37-dgA + RFB4 | 55.6 ± 10.5 (5) | 2 |
| HD37-dgA + HD37 | 50.2 ± 11.8 (5) | 2 |
| HD37-dgA + MOPC-21 | 53.6 ± 9.4 (5) | 2 |
| MOPC-21-dgA + MOPC-21 | 33.5 ± 1.9 (5) | 0 |
| MOPC-21-dgA + RFB4 | 34.6 ± 2.0 (5) | <1 |

[a]SCID mice were inoculated with $5 \times 10^6$ Daudi cells and treated either with a mixture of RFB4-dgA and HD37-dgA (20% of the $LD_{50}$ dose of each immunotoxin) or with different mixtures of either one of the immunotoxins (20% $LD_{50}$) and antibodies (equivalent amount) on days 1–4. Numbers in parentheses represent the number of mice per each group.
[b]Statistical significance of Table 5 as compared with Table 2:
(RFB4-dgA ± HD37-dgA) or (RFB4-dgA ± HD37) vs RFB4-dgA or HD37-dgA (20% $LD_{50}$): $p \leq 0.0001$
(RFB4-dgA ± RFB4) vs PBS: $p \leq 0.05$
RFB4-dgA (20% $LD_{50}$) vs (RFB4-dgA ± RFB4) $p \leq 0.05$
(RFB4-dgA ± MOPC-21) vs RFB4-dgA (20% $LD_{50}$) : $p > 0.05$
(HD37-dgA ± either RFB4, HD37 or MCPC-21) vs HD37-dgA (20% $LD_{50}$): $p > 0.05$
(MOPC-21-dgA + MOPC-21) vs PBS: $p > 0.05$
(MOPC-21-dgA ++ RFB4) vs RFB4 (20% $LD_{50}$): $p > 0.05$
[c]Extrapolated on paralysis curve (Ghetie et al., 1991)
[d]Average of two sets of studies
[e]Compare with data in Table 2

5. Macroscopic and Microscopic Evaluation of Organs from Treated Mice

No major differences were observed between the tumor burden or sites of tumor growth in mice treated with either one of the two immunotoxins or with cocktails with the possible exception of a reduced tumor burden in the ovaries of the mice treated with RFB4-dgA[2] as compared to HD37-dgA. Microscopic examination showed that the sites of tumor growth in the spinal canal were the same in mice treated with combination therapy as in untreated mice even though tumor developed much more slowly.

C. Discussion

The effect of combination therapy with immunotoxins or immunotoxins and antibodies has not been investigated in SCID mice with human lymphoma. However, a cocktail of three anti-T cell immunotoxins has been reported to perform better than single immunotoxins in vitro (Katz et al., 1987). Studies in nude mice have also shown that combinations of two immunotoxins directed against non-T ALL cells are more effective than single immunotoxins (Hara et al., 1988).

The results presented above demonstrate that, at 40% of the $LD_{50}$ dose, HD37-dgA was less effective than RFB4-dgA in extending the survival of mice. This result is consistent with the lower cytotoxic activity of HD37-dgA in vitro. Since the two immunotoxins had different effects at higher doses (40% of the $LD_{50}$ dose), but not at lower doses, (20% of the $LD_{50}$ dose) the optimal dose of a given immunotoxin may vary depending on the nature and density of the antigen which it recognizes on tumor cells and the mechanisms involved in cytotoxicity or cytostasis. In this regard, RFB4-dgA is more effective than HD37-dgA at killing Daudi cells in vitro as well even though these cells express similar densities of CD19 and CD22.

These data also show that at 40% of the $LD_{50}$ dose of HD37-dgA, or its equivalent in antibody, survival was prolonged only when the agents were administered early. It has previously been reported that an IgG2a anti-CD19 antibody only inhibited the tumor growth of Daudi lymphoma xenografts in nude mice when administered early after tumor inoculation, unless IL-2 was also given (Vuist et al., 1989). The anti-tumor effect might be a result of natural killer (NK) mediated ADCC. Thus, peritoneal exudate cells were able to inhibit the proliferation of Daudi cells in vitro in the presence of anti-CD19 antibody. Similarly, spleen cells preincubated with IL-2 induced ADCC against Daudi cells sensitized with anti-CD19 (Vuist et al., 1989). The same anti-CD19 antibody was administered to six patients with non-Hodgkin's lymphoma and one patient showed a partial remission (Hekman et al., 1991).

In contrast with the above studies, another anti-CD19 (B43) antibody did not show any anti-tumor effect in SCID mice with human t(4;11) cell leukemia (Jansen et al., 1992). This indicated to the inventors that HD37 antibody might not have the same anti-tumor effect on all CD19+ tumors or that the anti-tumor effect is dependent upon the epitope which the anti-CD19 antibody recognizes. In the present example, it is unlikely that ADCC or complement were involved in the anti-tumor effect of HD37, since $F(ab')_2$ fragments were also effective. An apoptotic mechanism has also been ruled out since the in vitro incubation of Daudi cells with various concentrations of HD37 does not induce characteristic DNA fragmentation. Therefore, the anti-tumor effect of the HD37 antibody may be due to a novel type of death similar to that described for an anti-IgM antibody on a human B-lymphoma cell line (Ishigami et al., 1992).

The cytostatic effect of HD37 might also be related to the reported inhibitory activity of several anti-CD19 antibodies, including HD37, (IgG or as Fab' fragment) on B-cell proliferation induced by anti-Ig antibody alone or in combination with B-cell growth factor (Pezzutto et al., 1987; DeRie et al., 1989; Rigley & Callard, 1991). It has been shown that anti-CD19 can arrest the entry of stimulated tonsilar B cells into S-phase by inhibiting DNA, but not RNA synthesis (Rigley & Callard, 1991). If anti-CD19 antibody can induce the same down-regulatory signal in Daudi cells, then it is possible that it blocks or impairs the proliferation of the tumor cell in vivo in the absence of effector cells in the host. It should be emphasized that Daudi cells respond to treatment with anti-CD19 by a rapid increase in intracellular $Ca^{2+}$ even though this effect has not been reported in normal B cells (DeRie et al., 1989).

In conclusion, the results presented herein indicate that the anti-tumor activity of combinations of anti-CD22-dgA and anti-CD19-dgA or anti-CD22-dgA and anti-CD19 antibody is better than that of any of these three agents alone. The finding that anti-CD19 and anti-CD22-dgA have enhanced anti-tumor activity suggests that combinations of antibodies and immunotoxins directed against different target antigens should be considered in designing future clinical trials with these reagents.

EXAMPLE III

Anti-CD19 Antibodies and Cell Cycle Arrest

A. Materials and Methods

1. Cells

Three Burkitt's lymphoma cell lines (Daudi, Namalwa, and Raji), one pre-B cell line (Nalm 6) and one diffuse histiocytic lymphoma cell line (DHL-4, obtained from Dr. Levy, Stanford) were maintained in culture by serial passage in RPMI 1640 medium containing 25 mM HEPES, 10% heat-inactivated fetal bovine serum, 100 U/ml penicillin, 100 µg/ml streptomycin (complete medium) and 100 mM L-glutamine. The cells were grown in a humidified atmosphere of 5% $CO_2$ and air. Daudi cells were used for i.v. inoculation of SCID mice ($5 \times 10^6$ cells/mouse). Cell viability was determined by trypan blue exclusion.

2. Antibodies

Mouse IgG1 mAbs specific for CD22 (RFB4) or CD19 (HD37, B43, 4G7, BU12) and the purified isotype-matched (IgG1) myeloma protein (MOPC-21) (control) were used. Both RFB4 and HD37 were obtained from Abbot Biotech/Repligen (Needham Heights, Mass.). The B43 Ab was obtained from Dr. F. Uckun, University of Minnesota. The 4G7 Ab and MOPC-21 myeloma protein were prepared by purification of cell supernatants (SNs) on a protein-A Sepharose column. The BU12 Ab was obtained from Dr. D. Flavell, University of Southampton, U.K.

3. Animals

Female SCID mice (C.B-17 SCID/SCID) were bred in the colony at the University of Texas. They were housed and maintained in a specific pathogen-free (SPF) facility. Animals were fed autoclaved food and sterile water ad libitum, and all manipulations were performed in a laminar flow hood.

4. SCID/Daudi Mice

SCID mice of 6–10 weeks of age were inoculated i.v. with $5 \times 10^6$ Daudi cells in 0.1 ml PBS. Mice were checked daily and were sacrificed at the onset of paralysis, a clinical symptom which accurately predicts death (Ghetie et al., 1990). The mean paralysis time (MPT) was taken as end point in this animal model (Example II and Ghetie et al., 1992). Complete necropsy and histopathologic examinations were done on animals that survived beyond a year. Tissue from lung, heart, liver, spleen, kidney, ovary and vertebrae were fixed in 10% buffered formalin, embedded in paraffin, sectioned and stained with hematoxylin and eosin.

5. Therapy of SCID/Daudi Mice

SCID mice were inoculated with Daudi cells 24 hours before treatment with HD37 Abs [IgG or $F(ab')_2$], ITs, or with cocktails of Abs and ITs as described previously in Example II. Groups of 5–7 mice were inoculated retroorbitally with a total amount of Ab equivalent to that used in the respective ITs (20% [60 µg], or 40% [120 µg] of the $LD_{50}$ dose) in a single course of four equal injections on days 1–4 after tumor inoculation. Other mice (5 per group) were treated with 3 different amounts of HD37 Ab (0.1, 1.0, or 5.0 mg per mouse) given on days 1–4 after tumor inoculation or with the following mixtures: 1) RFB4-dgA (60 μg)+HD37-dgA (60 μg); 2) RFB4-dgA (60 μg)+HD37 [IgG or F(ab')₂] [(50 μg, representing 20% LD₅₀ equivalent amounts of either IgG or F(ab')₂ or 500 μg, representing 200% LD₅₀ equivalent amounts of F(ab')₂)].

6. Adoptive Transfer

Mice surviving for one year were sacrificed. Cells from ovaries and spinal cords (Ghetie et al., 1990). were injected i.v. into healthy SCID mice as described above.

7. Preparation of F(ab')₂ and Fab Fragments of HD37

F(ab')₂ fragments of HD37 were obtained by digesting the IgG with pepsin as described by (Ghetie et al., 1988) and were purified by gel permeation high performance liquid chromatography (HPLC) using a preparative 21.5×600 mm TSK 3000SWG column (ULTROPAC (HPLC column) Pharmacia, Uppsala, Sweden). Fab fragment was obtained by digestion of the IgG with papain followed by purification on protein A-SEPHAROSE (gel filtration matrix) (Goding et al., 1983).

8. Immunotoxins (ITs)

HD37-dgA and RFB4-dgA were prepared as described by (Ghetie et al., 1998, Cancer Res.). The purity of the ITs was determined by electrophoresis under both nonreducing and reducing conditions on 7.0% sodium dodecyl sulphate-polyacrylamide gels and by gel permeation HPLC on an analytical 7.5×600 mm TSK 3000SW column (ULTROPAC (HPLC column) Pharmacia, Sweden). The IT preparation was 95% pure.

9. The Effect of Anti-CD19 on Cells In Vitro

The activity of different Abs [either intact IgG, F(ab')₂ or Fab' fragments] was determined using [$^3$H]-thymidine, [$^3$H]-leucine or [$^3$H]-uridine incorporation assays as described by Ghetie et al. (1998, Cancer Res.). In order to study the reversibility of the inhibitory activity, Daudi cells (1×10⁶/ml) were incubated in a 25 cm² tissue culture flask for 24–48 hours with different Abs at 300 μg/ml at 37° C. Cells were then plated in 96 well plates and pulsed with either [$^3$H]-leucine or [$^3$H]-thymidine. The remaining cells in each flask were washed and adjusted to a maintenance concentration of 4×10⁵/ml and cultured for 2–3 weeks. Twice a week the concentration, viability, and incorporation of [$^3$H]-leucine or [$^3$H]-thymidine were determined. The cells were fed 3 times a week with complete RPMI media. After the cells recovered in culture they were re-treated with Abs as described above and [$^3$H]-thymidine or [$^3$H]-leucine incorporation were again measured.

10. DNA Fragmentation Assay

2–5×10⁶ treated or untreated Daudi cells were collected by centrifugation and lysed in 0.2–0.5 ml hypotonic buffer (5 mM Tris-HCl, pH 7.4, 5 mM Na₂-EDTA, 0.5% TRITON X-100 (nonionic surfactant). The lysates were centrifuged and the SNs were deproteinated as described by Groux et al. (1992). The DNA extracts were analyzed on a 2% agarose gel, containing 0.0001% ethidium bromide.

11. Binding of Iodinated HD37, 4G7, BU12, and B43 Abs to CD19 on Daudi Cells

Daudi cells (1×10⁷/ml) were incubated at 4° C. for 3 hours with various concentrations of iodinated Abs as described by Ghetie et al. (1998, Cancer Res.). The affinity constant (K) and the number of Ab molecules bound per cell (n) under conditions of equilibration were calculated by using the Scatchard form of the equilibrium equation (Trucco et al., 1981). For cross-blocking experiments the four anti-CD19 Abs were incubated with Daudi cells (1×10⁷/ml) using a constant concentration of either one of the above radiolabeled Abs (0.5 μg/ml/10⁷ cells) in the presence of 40-fold higher concentrations of each cold Ab (20.0 μg/ml/10⁷ cells). The 50% inhibition of binding was calculated for each Ab.

12. Analysis of Cell Cycle Progression

Cells were simultaneously examined for viability and cell cycle status by flow cytometric analysis using the DNA-binding dyes 7-amino actinomycin D (7-ADD) and Hoechst 33342 (both from Molecular probes; Eugene, Oreg.). 1×10⁶ Daudi cells were incubated for 24 hours at 37° C. either with media (control) or with different Abs as described above, were washed twice with 10% FCS-containing RPMI-1640 media and the cell pellet was treated with 50 μl of 400 μM 7-AAD and incubated on ice for 30 minutes (7-AAD acting as a vital dye). Cells were then fixed (1.0 ml of 0.5% paraformaldehyde in PBS), and simultaneously permeabilized and stained with the Hoechst dye (220 μl of Hoechst at 10 μg/ml in 5% TWEEN-20 (non-ionic detergent) overnight at 4° C. After filtration through 50 μm nylon mesh, samples were analyzed on a dual laser/pulse processor-equipped FACStar (Becton Dickinson) (10⁵ cells/analysis). After gating on single, viable cells (viable cells are 7-ADD-negative and aggregates were excluded using an area vs. width plot of the Hoechst signal) the percent of cells in each stage of the cell cycle was determined using the Paint-A-Gate program.

B. Results

1. Effects of HD37 and RFB4 Abs in SCID/Daudi Mice

Both RFB4 (anti-CD22) and HD37 (anti-CD19) prolong the survival of SCID/Daudi mice as determined by MPT (Table 6). At two doses, the anti-tumor activity of RFB4 vs. PBS (control) was at the limit of significance whereas the anti-tumor activity of HD37 was highly significant. The ability of HD37 to prolong the survival of SCID-Daudi mice was dose-dependent (Table 6); the highest dose of Ab (5 mg) was well tolerated and prolonged survival to a degree consistent with 5–6 logs of tumor cell depletion (Example II and Ghetie et al., 1992).

TABLE 6

In vivo Effect of HD37 and RFB4 Abs on Survival of SCID/Daudi Mice

| Ab[a] | μg Administered[b] | MPT ± S.D. (Days) |
|---|---|---|
| PBS (Control) | — | 30.6 ± 2.3 (5) |
| MOPC-21 (Control) | 100 | 26.0 ± 1.7 (5) |
| RFB4 (anti-CD22) | 50 | 38.4 ± 5.6 (5) |
| HD37 (anti-CD19) | 50 | 43.6 ± 3.7 (5) |
| RFB4 | 100 | 46.2 ± 7.3 (5) |
| HD37 | 100 | 57.8 ± 6.1 (8) |
|  | 1,000 | 72.3 ± 7.6 (4) |
|  | 5,000 | 113.8 ± 17.5 (5) |

[a]SCID mice were inoculated with 5 × 10⁶ Daudi cells and were treated either with RFB4 or HD37Abs on days 1-4 after tumor inoculation. Untreated animals or animals treated with MOPC-21 (IgG1 isotype-matched Ab) were used as controls.
[b]Dose injected was equivalent to 40% or 20% of the LD₅₀ dose of ITs for all Abs but HD37 for which two additional higher doses were also tested.
[c]Mean paralysis time (MPT) was taken as the end point in the experiment[24]. Numbers in parentheses represent the number of mice per group.
Statistical significance (estimated by using EPISTAT program) are as follows:
RFB4: (50 μg) vs. PBS: p = 0.0656; (100 μg) vs. PBS: p = 0.0325
HD37: (100 μg) vs. PBS: p = 0.0000023; (50 μg) vs. PBS: p = 0.0025
HD37: (100 μg) vs. RFB4 (100 μg): p = 0.0084
HD37: (50 μg) vs. RFB4 (50 μg): p = 0.3976

2. The Inhibition of Tumor Growth by HD37 is Fc-independent

In previous studies, the inventors demonstrated that both the intact and F(ab')₂ forms of HD37 were as effective as HD37-dgA in extending the survival of SCID/Daudi mice (Example II and Ghetie et al., 1992). Since the T₁/₂ of F(ab')₂ in SCID mice is 10-fold shorter than that of intact IgG, the effect of treating SCID/Daudi mice with two different "cocktails" was compared: (A) RFB4-dgA (20% of $LD_{50}$)+HD37-F(ab')$_2$ (equivalent to 20% of Ab in an $LD_{50}$ dose of IT), and (B) RFB4-dgA (20% of $LD_{50}$)+HD37-F(ab')$_2$ (equivalent to 200% of Ab in an $LD_{50}$ dose of IT, in order to offset the shorter $T_{1/2}$).

Figure 2A:
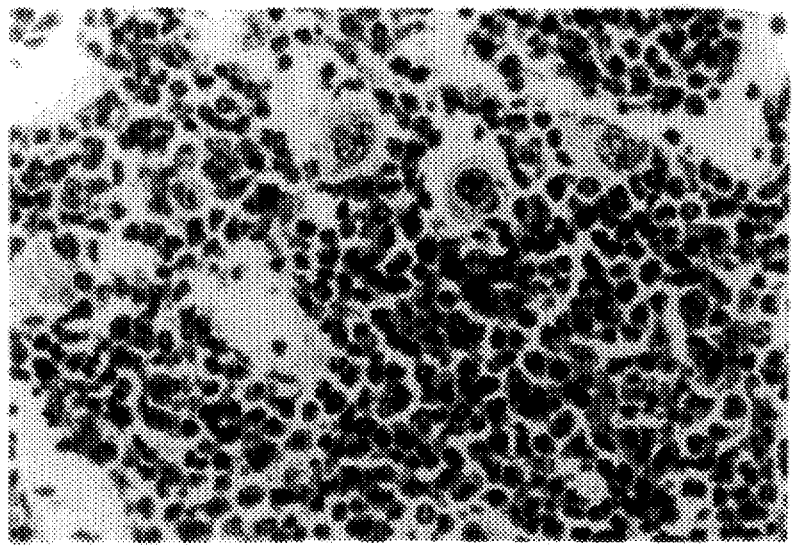
FIG. 2A. Vertebral marrow from a mouse inoculated with Daudi cells and treated with [RFB4-dgA+200% HD37-F(ab')$_2$] and sacrificed at 367 days post inoculation. Note normal megakaryocytic, myelocytic and erythrocytic differentiation of hematopoietic cells (original magnification 400×).
Figure 2B:
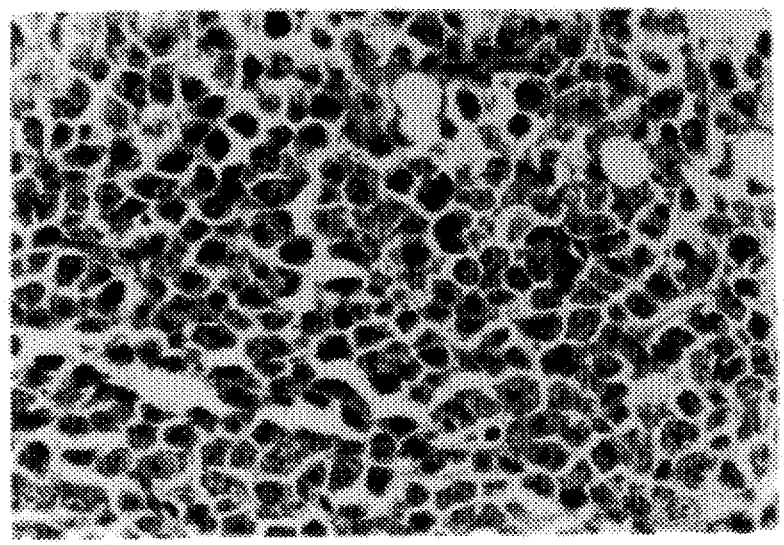
FIG. 2B. Vertebral marrow from a control mouse inoculated with Daudi cells and sacrificed at day 29 post inoculation. A monomorphic population of Daudi cells replaces the hematopoietic cells (original magnification 400×).

Treatment with cocktail A extended the MPT significantly (101.0±30.3 days) and treatment with cocktail B cured the mice, i.e., all mice (5) in this group survived over 1 year (FIG. 1) with no signs of tumor growth (namely, paresis or paralysis of hind legs). After 1 year the mice were sacrificed and gross and histological examinations were performed. No tumors were identified in any of the mice (FIG. 2). Adoptive recipients of cells from ovaries and spinal cords obtained from 1 year survivors showed no evidence of tumors 150 days later, demonstrating that the cells were free of dormant tumor cells. Hence, the anti-tumor effect of HD37 Ab is Fc-independent indicating that ADCC is not involved. When compared with the results in Table 6, it was concluded that large amounts of HD37 Ab alone are insufficient to cure the mice, but that in combination with the RFB4 IT, HD37 can completely inhibit tumor growth.

3. In Vitro Effect of Different Anti-CD19 Abs and Their Fragments

Figure 3:
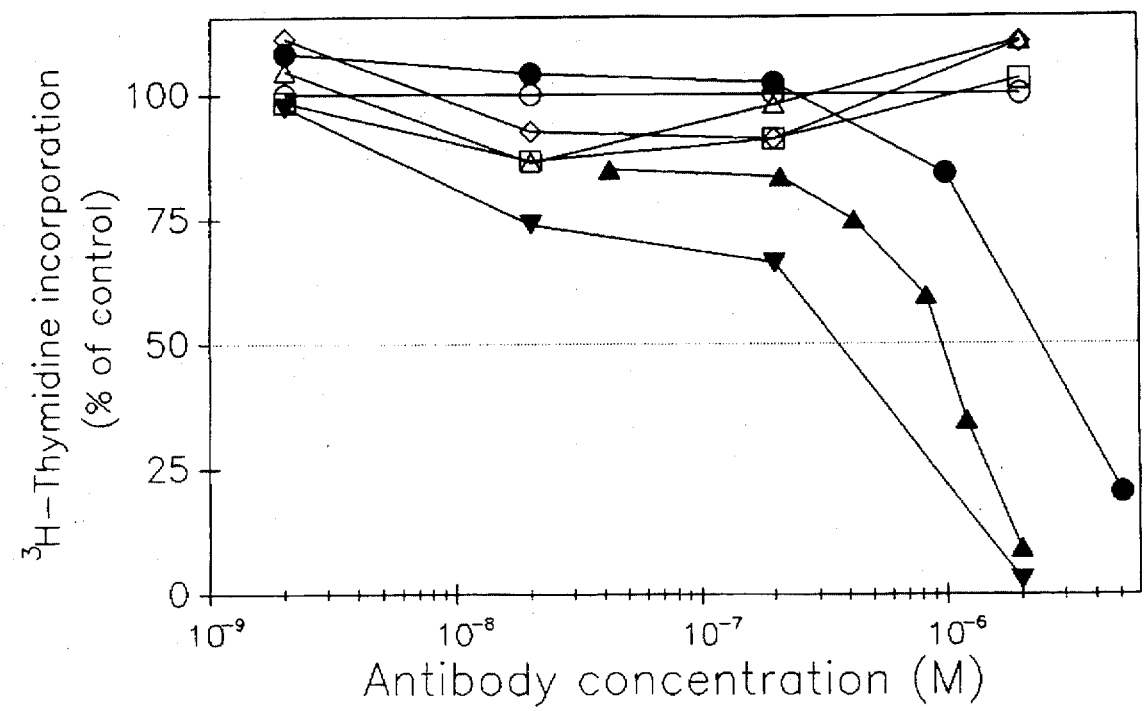
FIG. 3. [$^3$H]-thymidine incorporation in Daudi cells pretreated with different Abs. Daudi cells ($1 \times 10^5$/well/100 µl) were incubated with different concentrations of Abs ($1 \times 10^{-9}$ to $1 \times 10^{-6}$M) for 24 hours, then pulsed with [$^3$H]-thymidine for 18 hours, harvested and counted. The reduction in incorporation in cells treated with Abs (% of control) was plotted against the concentration: —△— MOPC-21; —□— RFB4; —▼— HD37 (IC$_{50}$=5.2±2.5×10$^{-7}$M); —◇— B43; —●— 4G7 (IC$_{50}$=8.9±2.0×10$^{-7}$M); —▲— BU$_{12}$ (IC$_{50}$=5.1±0.2×10$^{-7}$M). This is the mean±S.D. of 3 studies.

The effects of different anti-CD19 Abs [HD37, B43, 4G7, BU12 (all IgG$_1$)] on proliferation of Daudi cells in vitro were next compared. HD37, BU12 and 4G7 inhibited the incorporation of [$^3$H]-thymidine with an average IC$_{50}$ of 5.2±2.5×10$^{-7}$M (HD37), 5.1±0.2×10$^{-7}$M (BU12) and 8.9±2.0×10$^{-7}$M (4G7) (FIG. 3). However, despite the fact that HD37 and BU12 had similar IC$_{50}$'s, BU12 was more effective at killing Daudi cells; at 2×10$^{-6}$M BU12 killed over 90% of the cells, whereas HD37 and 4G7 (at the same concentration) killed only 60%. Therefore, in order for 4G7 and HD37 to kill as effectively as BU12, three-fold more HD37 or 4G7 was necessary (FIG. 3).

B43-anti-CD19, RFB4-anti-CD22 and an isotype-matched control (MOPC-21) had no effect on Daudi cells at any concentration tested. The same pattern of inhibition was observed using [$^3$H]-leucine or [$^3$H]-uridine incorporation assays. The viability of cells treated with different concentrations of HD37 was also examined. The effect of F(ab')$_2$ and Fab fragments of HD37 on Daudi cells was also compared. The former had the same inhibitory activity as IgG and the latter had no effect at concentrations up to 500 µg/ml.

4. The In Vitro Effect of Anti-CD19 on Different Cell Lines

Figure 4:
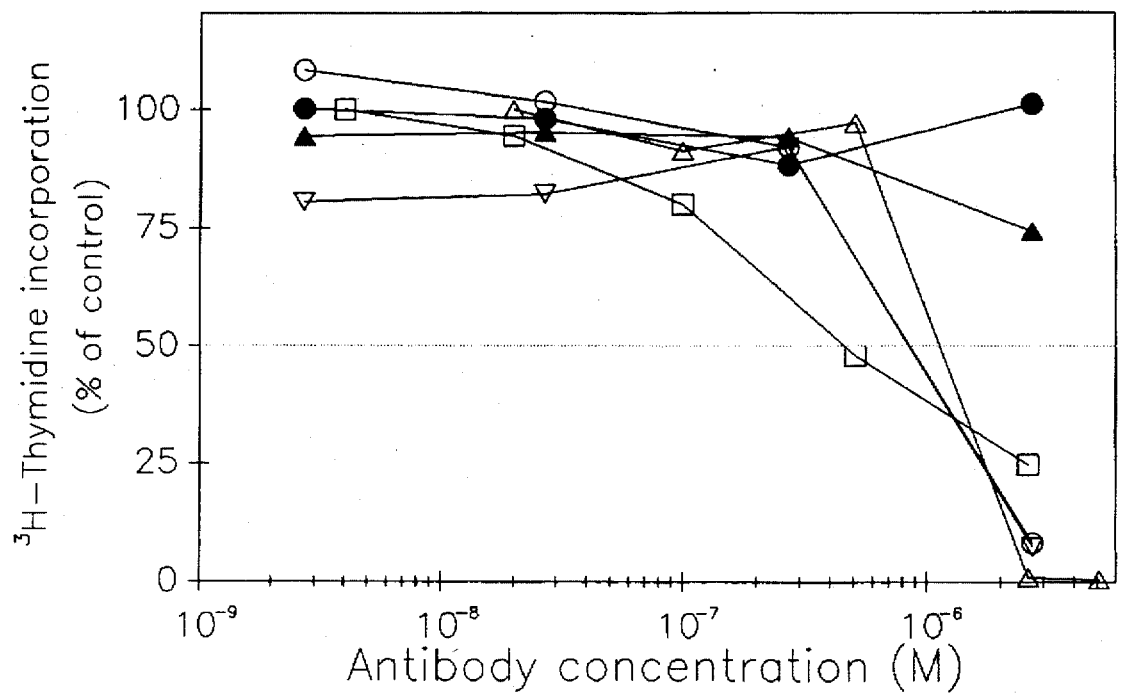
FIG. 4. [$^3$H]-thymidine incorporation in different cell lines pre-treated with HD37 Ab: —○— Daudi (IC$_{50}$=5.2±2.5×10$^{-7}$M); —△— Raji (IC$_{50}$=9.8±3.2×10$^{-7}$M); —▽— Namalwa (IC$_{50}$=8.4±2.1×10$^{-7}$M); —□— DHL-4 (IC$_{50}$=3.3±1.5×10$^{-7}$M); —▲— Nalm-6; —●— Jurkat. This is the mean±S.D. of 3 studies.

It was determined whether the anti-CD19-mediated inhibitory effects were unique to the Daudi cell line. For this purpose, two other CD19$^+$ Burkitt's lymphoma cell lines (Raji, and Namalwa), a CD19$^{lo}$ pre-B cell line (Nalm-6), a CD19$^+$ diffuse histiocytic lymphoma cell line (DHL-4), and a CD19$^-$ T-leukemia cells (Jurkat) were tested. The growth of the CD19$^+$ Burkitt's lymphoma cell lines and the CD19$^+$ diffuse histiocytic lymphoma was inhibited by HD37 whereas the growth of the CD19$^{lo}$ and CD19$^-$ cell lines was not (FIG. 4). Hence, CD19-mediated growth inhibition is dependent upon the expression of a sufficient density of CD19 on the tumor cells and appears not to be restricted to Burkitt's lymphomas.

5. Does HD37 Induce Apoptosis and/or Cell Cycle Arrest?

Figure 5:
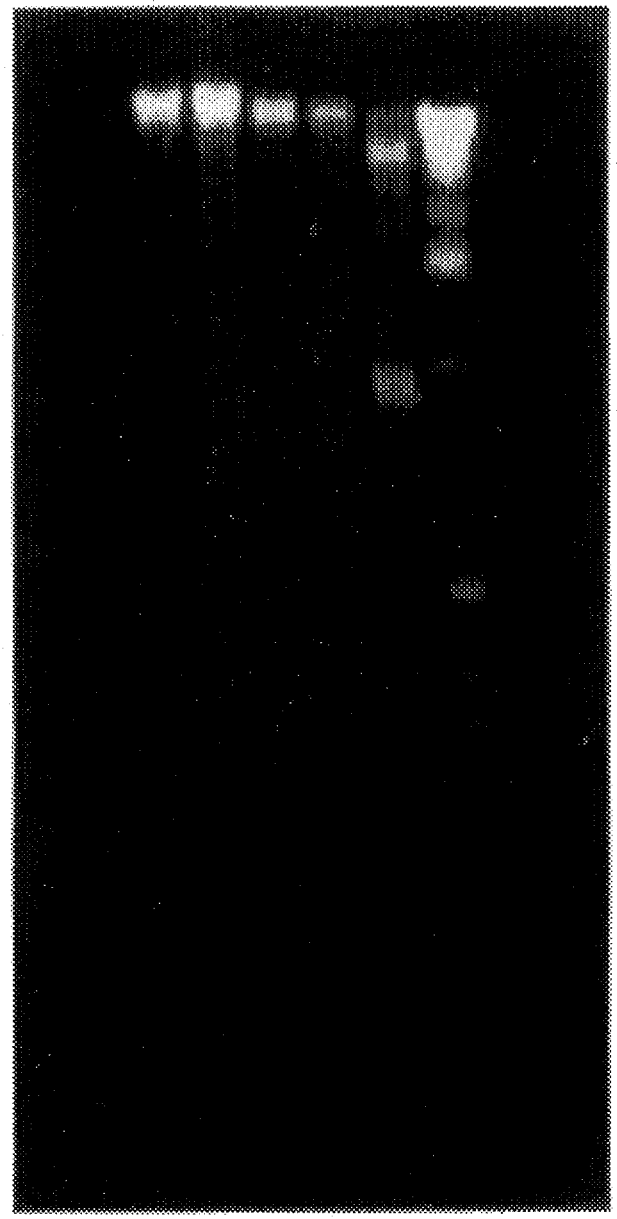
FIG. 5. 2% agarose gel of DNA isolated from Daudi cells lane 1: untreated; lane 2: HD37-treated; lane 3: BU12-treated; lane 4: RFB4-treated. [Daudi cells ($1 \times 10^7$ cells/ml) were incubated with the above Abs at a concentration of $2 \times 10^{-6}$M for 24 hours at 37° C.]; lane 5: incubated at 42° C. for 30 minutes then over night at 37° C. (mild hyperthermia as a positive control for apoptosis)$^{45}$ The apoptotic Daudi cells (lane 5) showed significant inhibition (50–60%) of $^3$H-thymidine incorporation; lane 6: DNA ladder.

It was next determined whether the inhibitory effect of anti-CD19 was due to apoptosis or cell cycle arrest. None of the Abs tested caused detectable DNA fragmentation, indicating that anti-CD19 and anti-CD22 do not induce apoptosis during a 24 hour incubation (FIG. 5). By contrast, anti-CD19 induces cell cycle arrest.

Figure 6:
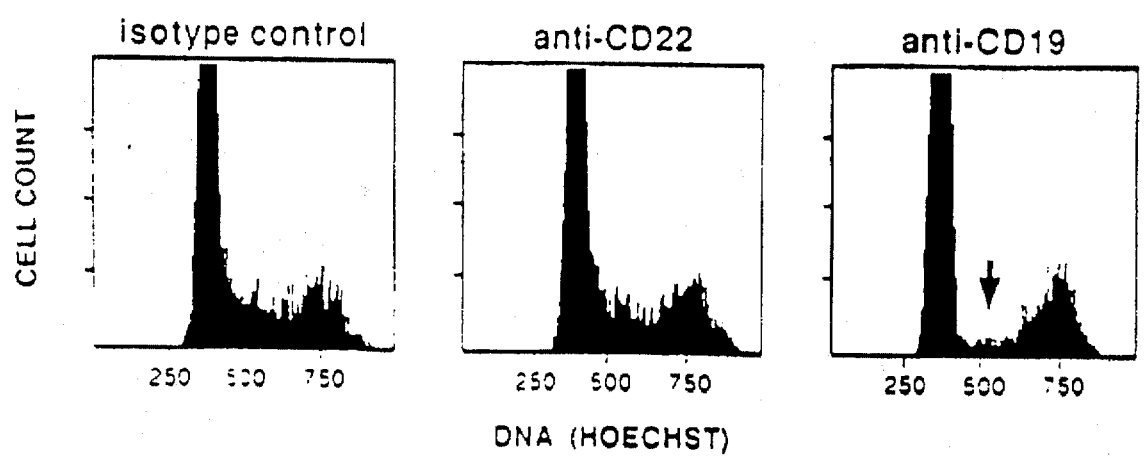
FIG. 6. FACS analysis of the DNA in 4000 viable Daudi cells. Samples cells incubated overnight at 37° C. with different Abs [isotype IgG$_1$, MOPC-21; anti-CD22 (RFB4) or anti-CD19 (HD37)] were stained with Hoechst dye and were analyzed on a dual laser/pulse processor-equipped FACStar (Becton Dickinson). A representative example of cell cycle progression analysis. The reduction of the percent of cells in S phase after incubation with anti-CD19 Ab is indicated by the arrow.

FIG. 6 shows a representative FACS profile and Table 7 summarizes the data concerning cell cycle progression and the percentage of viable cells in different stages of the cell cycle after a 24 hour incubation either with medium (control) or different Abs. The data demonstrate that the HD37, BU12 and 4G7 Abs induce a decrease in the number of cells in S-phase with accumulation of cells in the $G_1$ phase of the cell cycle. The number of cells in G2/M phases of the cell cycle remains essentially unchanged. The RFB4-anti-CD22 and the isotype-matched irrelevant IgG1 (MOPC-21) had no effect. The reduction in the number of cells in S phase is consistent with the ability of these Abs to inhibit $^3$H-thymidine incorporation (Table 7). Taken together, these observations support the occurrence of cell cycle arrest in the $G_1$ phase of the cell cycle, and perhaps G2/M.

TABLE 7

The Effect of Different Abs on Cell Cycle Progression and $^3$H—Thymidine Incorporation[a]

| Treatment[b] | Specificity | Incorporation Percent of Cells in cell cycle phases | | | $^3$H—Thymidine (% of control) |
|---|---|---|---|---|---|
| | | G0/G1 | S | G2 | |
| PBS (Control) | — | 62.5 ± 2.8 (3) | 18.1 ± 1.5 (3)[c] | 19.4 ± 4.0 (3) | 100.0 ± 0.0 (3) |
| HD37 | CD19 | 71.8 ± 1.1 (3) | 8.8 ± 1.6 (3) | 19.4 ± 0.4 (3) | 22.1 ± 9.5 (3) |
| BU12 | " | 74.7 ± 3.5 (3) | 3.7 ± 0.4 (3) | 21.9 ± 3.8 (3) | 3.4 ± 0.4(3) |
| 4G7 | " | 67.0 (1) | 13.4 (1) | 19.6 (1) | 40.1 (1) |
| B43 | " | N.D. | N.D. | N.D. | 91.1 (1) |
| RFB4 | CD22 | 66.6 ± 2.5 (3) | 15.4 ± 0.9 (3) | 18.0 ± 3.4 (3) | 96.6 ± 3.0 (3) |
| MOPC-21 | None | 65.0 ± 3.2 (3) | 15.0 ± 1.7 (3) | 17.6 ± 2.7 (3) | 89.2 ± 6.0 (3) |

[a]Daudi cells (1 × 10$^6$/ml) were incubated with the above Abs (at a concentration of 2 × 10$^{-6}$ M) for 24 hours at 37° C. Aliquots of cells were stained with 7-AAD and Hoechst and analyzed in a FACStar or were pulsed with $^3$H—thymidine and analyzed in a β-counter.
[b]All IgG$_1$
[c]Number in parentheses represents the number of studies performed.

6. Binding of Anti-CD19 Abs to Daudi Cells

It was next determined whether the CD19-mediated anti-tumor effect was related to the affinity or epitope specificity of a particular Ab. The affinity constant of each of the anti-CD19 Abs (HD37, B43, BU12 and 4G7) was determined and it was found that HD37, B43 and 4G7 have similar affinities ($3.6\pm1.2\times10^8$ $M^{-1}$) and that BU12 has a 3-fold higher affinity ($1.1\pm0.3\times10^9$ $M^{-1}$). The number of Ab molecules bound to Daudi cells was also similar ($10^5$ molecules/cell) for three anti-CD19 Abs (HD37, B43 and 4G7). Cross-blocking experiments demonstrated that all the anti-CD19 Abs recognize the same or adjacent epitopes on the CD19 antigen (Table 8). Clearly the BU12 antibody which has the highest affinity, also induces cell cycle arrest most effectively. It is unclear why B43 is ineffective, but it is possible that it recognizes an adjacent, but slightly different epitope as suggested by the cross-blocking data.

TABLE 8

Cross-blocking of different anti-CD19 Abs on Daudi Cells

| Ab | | Inhibition of binding | Affinity constant |
|---|---|---|---|
| Unlabelled | $^{125}$I-Labeled | (%)$^a$ | ($Ka \times 10^8 M^{-1}$) |
| HD37 | HD37 | $92.0 \pm 3.0$ | $3.6 \pm 0.2$ (3) |
| B43 | B43 | (3) | $2.3 \pm 0.4$ (3) |
| 4G7 | 4G7 | 74.8 (2) | 2.5 (2) |
| BU12 | BU12 | $94.7 \pm 3.2$ (3) | $11.0 \pm 0.3$ (3) |
|  |  | 89.4 (2) |  |
| HD37 | B43 | 85.1 (2) | — |
| B43 | HD37 | 81.8 (2) | — |
| HD37 | 4G7 | $94.2 \pm 3.0$ (3) | — |
| 4G7 | HD37 | $96.1 \pm 2.1$ (3) | — |
| HD37 | BU12 | 91.8 (2) | — |
| BU12 | HD37 | 93.5 (2) | — |

$^a$Daudi cells ($1 \times 10^7$/ml) were incubated with a constant concentration of either one of the above radiolabeled anti-CD19 Abs (0.5 µg/ml/$10^7$ cells) in the presence of a 40 fold excess of each unlabeled Ab (20 µg/ml/$10^7$ cells). The percent inhibition was calculated for each pair of antibodies. The number in parenthesis represents the number of studies performed.

C. Discussion

The major findings to emerge from these studies are as follows: 1) Anti-CD19 Ab (HD37) or its F(ab')$_2$ fragments inhibit the growth of disseminated human Burkitt's lymphoma in SCID mice and in combination with an anti-CD22 IT is curative in early disease. The anti-tumor activity of HD37 is dose-dependent. 2) Anti-CD19 causes cell cycle arrest in tumor cells expressing high levels of CD19. 3) Inhibition of cell proliferation by anti-CD19 Abs requires cross-linking and is dependent upon the affinity of the Ab. These data indicate that ligation of CD19 by the appropriate anti-CD19 Ab on lymphoma cells can transduce a negative growth signal.

In previous studies, the inventors have demonstrated that disseminated growth of Daudi cells in SCID mice was inhibited by treatment with ITs resulting in a prolongation of survival (Ghetie et al., 1991). A combination of two ITs (anti-CD22-dgA and anti-CD19-dgA) showed increased effects. The anti-tumor activity of an anti-CD22-IT was also markedly enhanced by an anti-CD19 Ab (not conjugated to dgA) (Example II and Ghetie et al., 1992). As shown in the present example, when higher doses of HD37 were administered (500 µg/mouse) in combination with an anti-CD22-IT, tumor growth was completely prevented. Importantly, when F(ab')$_2$ fragments of HD37 were injected in 10-fold higher doses (to offset the 10-fold shorter $T_{1/2}$) in combination with the anti-CD22-IT, the mice were also cured. In contrast, mice were not cured by either the IT alone (Ghetie et al., 1991) or by HD37 alone, even at very high doses (5 mg/mouse). These results demonstrate an increased anti-tumor effect via two different mechanisms—one mediated by a potent toxin that inhibits protein synthesis and another by an Ab that induces cell cycle arrest.

These results are in agreement with in vivo findings (Vuist et al., 1989), where another anti-CD19 Ab (CLB-CD19) had marked ADCC-independent anti-tumor activity in vivo on Daudi cells grown in nude mice. Other studies have shown that treatment of six patients with B cell lymphoma with high doses (225–1000 mg) of IgG2a anti-CD19 induced two partial remissions in one patient; the second remission lasted over 9 months (Hekman et al., 1991). These authors did not comment on the relationship between the clinical response, the density of CD19 on the tumor cells from the different patients and the ability of the Ab to inhibit the growth of the tumor cells in vitro. A dose-dependent effect of other B cell-reactive Abs such as anti-CD21, anti-CD24 and anti-CD23 on an EBV$^+$ B cell tumor grown in SCID mice has also been described (Durandy et al., 1992) but the mechanisms were not explored. CAMPATH-1, another lymphocyte-reactive Ab, has also induced remission in patients with lymphoma, presumably by ADCC (Dyer et al., 1989).

The critical in vivo finding that distinguishes the present results from these earlier ones is the observation that F(ab')$_2$ anti-CD19 Ab appears as effective as intact anti-CD19 Ab in its anti-tumor activity. This suggests that a signal transduction mechanism is involved, and that classical humoral effector mechanisms are not playing a major role. These observations are also in accord with results of earlier studies using the murine BCL$_1$ lymphoma in which dormancy was induced with anti-Id (Dyke et al., 1991). The isolated dormant lymphoma cells were shown to be in cell cycle arrest with other physiological changes as well (Yefenof et al., 1993). Along these lines the result of anti-Id treatment of B cell lymphoma in humans are of particular interest. Significant anti-tumor effects have been achieved by such Abs independent of isotype suggesting that signal transduction mechanisms may be involved (Meeker et al., 1985; Brown et al., 1989).

These in vitro results confirm and extend the in vivo results described above. Thus, particular anti-CD19 Abs can inhibit DNA, RNA and protein synthesis and induce cell cycle arrest. These inhibitory effects are specific since neither anti-CD22 nor an isotype-matched irrelevant IgG$_1$ had these effects. These finding are explained by the fact that CD19 is intimately involved in the IgM signal-transduction complex. Signaling from cross-linked IgM is known to involve phosphorylation by Src family kinases and a series of second messengers (Cambier et al., 1993; DeFranco et al., 1992; Law et al., 1993), but the signaling pathways are just beginning to be defined. Regardless, cross-linking of IgM on B lymphoma cells in vitro can cause cell cycle arrest and apoptosis (Yao et al. 1993). Interestingly, apoptosis in the short term in vitro studies was not observed. Recently, the inventors have obtained evidence in murine lymphoma cells that the pathways for inducing apoptosis and cell cycle arrest may diverge at some point in the intracellular signaling cascade (Example IV). Thus, anti-CD19 acts by a different mechanism than anti-apo-1/Fas Abs which induce apoptosis and may represent only one signaling pathway of the Ig-complex.

There is a requirement for a high concentration of anti-CD19, far above that needed to cross-link all CD19 molecules on the target cells. This is consistent with other Abs, e.g., anti-CD20 (Press et al., 1987) and may be related to the requirement for repeated rounds of binding (CD20) and subsequent cross-linking (CD19) of the target antigens. Alternatively, the effects of anti-CD19 might be mediated by the cross-linking of CD19 to TAPA-1 since anti-TAPA-1 Abs have anti-proliferative effects on B lymphomas. Hence, high concentrations of anti-CD19 may be necessary for CD19 to engage TAPA-1 which is then responsible for the signaling. Neither anti-CD19 nor anti-CD20 induces [$Ca^{2+}$] fluxes as detected by flow cytometry.

In the studies reported here, three anti-CD19 Abs, (HD37, 4G7 and BU12), had similar effects, but another anti-CD19 Ab, B43, was not effective. The latter is consistent with the failure of B43 to induce an antitumor response in mice, unless conjugated to a ribosome-inactivating protein (Jansen et al., 1992). The inhibitory effect of different anti-CD19 Abs requires cross-linking and appears to be related to the affinity of the antibody and possibly to its epitope-specificity. The inhibitory effect of HD37 Ab was not restricted to Burkitt's lymphoma cell lines but was also observed using a $CD19^+$ diffuse histiocytic lymphoma. In any case, in vitro analysis of the effects of anti-tumor Abs will facilitate the selection of those Abs that can mediate negative signals. It is envisioned that this will lead to the development of more rational Ab-mediated therapies for lymphomas and perhaps other tumors.

Conventional approaches to the treatment of B cell lymphomas have emphasized the use of cytotoxic agents. These can cure about 30–50% of high grade lymphomas and typically none of low grade lymphomas. It is noteworthy that in the present studies, a combination of a cytotoxic agent (a cell reactive immunotoxin) and an antibody that induces cell cycle arrest show additive anti-tumor effects, this should therefore be utilized in the design of treatment for B cell tumors.

EXAMPLE IV

Lyn Signals Cell Cycle Arrest

Cross-linking of mIg on both murine $BCL_1$ and human Daudi cells initiates a cascade of signals leading to the induction of both apoptosis and cell cycle arrest in vitro. Using antisense oligonucleotides the inventors demonstrate that the Ig-associated Lyn tyrosine kinase is required for anti-Ig-mediated cell cycle arrest, but is not required for the signal leading to apoptosis. These results define a branch-point in the cytosolic signaling pathways mediating cell cycle arrest and apoptosis. In Daudi, Lyn is also critical for cell cycle arrest induced by CD19 signaling. Thus, the Lyn tyrosine kinase is proposed to be an important mediator of cell cycle arrest in neoplastic B lymphocytes and, perhaps, other cell types.

Analysis of the effect of anti-CD19 antibody on human B cell lymphoma suggests that the CD19 membrane molecule might send similar signals. Since the $F_c$ portion of the anti-CD19 is not required for potent anti-tumor effects in vivo, and since cross-linking of CD19 results in cell cycle arrest in vitro, the effectiveness of anti-CD19 antibodies in preventing tumor growth probably results from a signal transduction phenomenon similar to that observed for anti-Ig on $BCL_1$, rather than a classical antibody-mediated effector function, e.g. ADCC.

Anti-Ig induces an anti-proliferative response in a subclone of $BCL_1$, $BCL_1.3B3$, and the induction of cell cycle arrest and apoptosis. Treatment of $BCL_1.3B3$ cells with specific antisense oligonucleotides results in the depletion of the Lyn tyrosine kinase protein. When depleted cells are challenged with anti-Ig, apoptosis is still induced, but cell cycle arrest is not. The same result is observed in an anti-Ig treated lymphoma cell (Daudi). In addition, antisense lyn can prevent cell cycle arrest induced by the cross-linking of CD19. These results indicate that the Lyn tyrosine kinase is required for transduction of the cell cycle arrest signal initiated by cross-linking of mIg or CD19.

A. Materials and Methods

1. Antibodies and Antisense Oligonucleotides $BCL_1.3B3$ cells were cultured in RPMI with 5% FCS. Antibody preparations (7,8,10,11) were affinity purified and included rabbit anti-ovalbumin (35 µg/ml), rabbit anti-$BCL_1$ idiotype (35 µg/ml), goat anti-human IgM (7.5 µg/ml), goat anti-ovalbumin (7.5 µg/ml) and anti-CD19 (HD37; 350 µg/ml).

Cells were plated with antisense oligonucleotides 24 hrs before the addition of antibody. Oligonucleotides were phosphorothioate derivatives synthesized by Oligos Etc. Inc. (Wilsonville, Oreg.). For the $BCL_1.3B3$ cell experiments the sequences TGGATCCGACATGTCAGA (AS C1) (SEQ ID NO:1), CATCCTTGCAGGGCTTCAGT (AS C2) (SEQ ID NO:2), CATTATCCAAGCTCCCAAAT (AS C3) (SEQ ID NO:3), and CATATTTCTCGCTCGTGGTG (AS lyn) (SEQ IN NO:4) targeted the translation initiation regions of nonsense, blk, fyn, and lyn of mouse, respectively. For the Daudi experiments the sequences CATATTTC-CCGCTCGCGTGA (AS hulyn1) (SEQ ID NO:5) and CCT-TGTTCCTCTGGATCTTT (AS hulyn2) (SEQ ID NO:6) targeted the translation initiation region and an internal coding region of the human lyn gene, respectively. In addition to the phosphorothioate modification, AS hulyn2 contains a cholesterol modification at the 5' end to facilitate cellular uptake. A similarly modified oligonucleotide (AS C4) was used as a control for this reagent.

2. $^3$H-thymidine Incorporation

Cells ($3 \times 10^4$) were incubated at 37° C. for 8 hrs with antibody in 0.2 ml of medium before the addition of 1 µCi $^3$H-thymidine. Cells were harvested following a 16 hr pulse. All values are the mean of triplicate samples.

3. DNA Fragmentation

Cells ($10^6$) were plated with or without 0.67 µM antisense oligonucleotides in 1.5 ml medium and incubated for 24 hrs. at 37° C. before the addition of 150 µg antibody in 3.0 ml medium. After an additional 24 hrs. incubation, cells were treated with proteinase K (1 mg/ml) in 50 mM Tris/HCl pH 8.0, 100 mM NaCl, 100 mM EDTA, 1% (w/v) SDS, and the DNA was isolated by phenol:$CHCl_3$ (1:1) extraction and ethanol precipitation. DNA isolated from $3 \times 10^5$ cell equivalents was treated with RNaseA (1 mg/ml final) and resolved in 2% agarose gels with 1×TAE Buffer.

4. Flow Cytometric Analysis

Cells ($10^6$) were stained with the vital dye 7-amino actinomycin D (7-AAD; 400 µM in PBS) at 4° C. for 30 min., fixed with paraformaldehyde (0.5% w/v in PBS), permeabilized with TWEEN-20 (non-ionic detergent) (5% w/v in PBS), and then stained with the DNA-binding dye Hoechst 33342 (10 µg/ml in PBS; Sigma) for 16 hrs. Cells were analyzed by flow cytometry on a FACStar Plus equipped with UV excitation.

5. Immunoblots $BCL_1.3B3$ cells ($10^6$) in 4.5 ml of medium were treated with antisense oligonucleotides at 0.67 µM for 24 hrs. Cells were harvested, washed with PBS and resuspended in 20 µl of lysis buffer containing 20 mM Tris/HCl pH 8.3, 150 mM NaCl, 2 mM EDTA, 200 µM sodium orthovanadate, 50 mM sodium fluoride, 10 mM CHAPS. Following incubation for 30 min. at 4° C., nuclei were removed by centrifugation. Samples were resolved on a 9% SDS-polyacrylamide gel and proteins transferred to nitrocellulose filters. Immunoblots were prepared by chemiluminescence with affinity purified rabbit antiserum against a Lyn peptide (obtainable from J. Cambier, Denver, Colo.) and goat anti-rabbit alkaline phosphatase as described by the manufacturer (Biorad, Richmond, Calif.).

B. Results

Figure 7A:
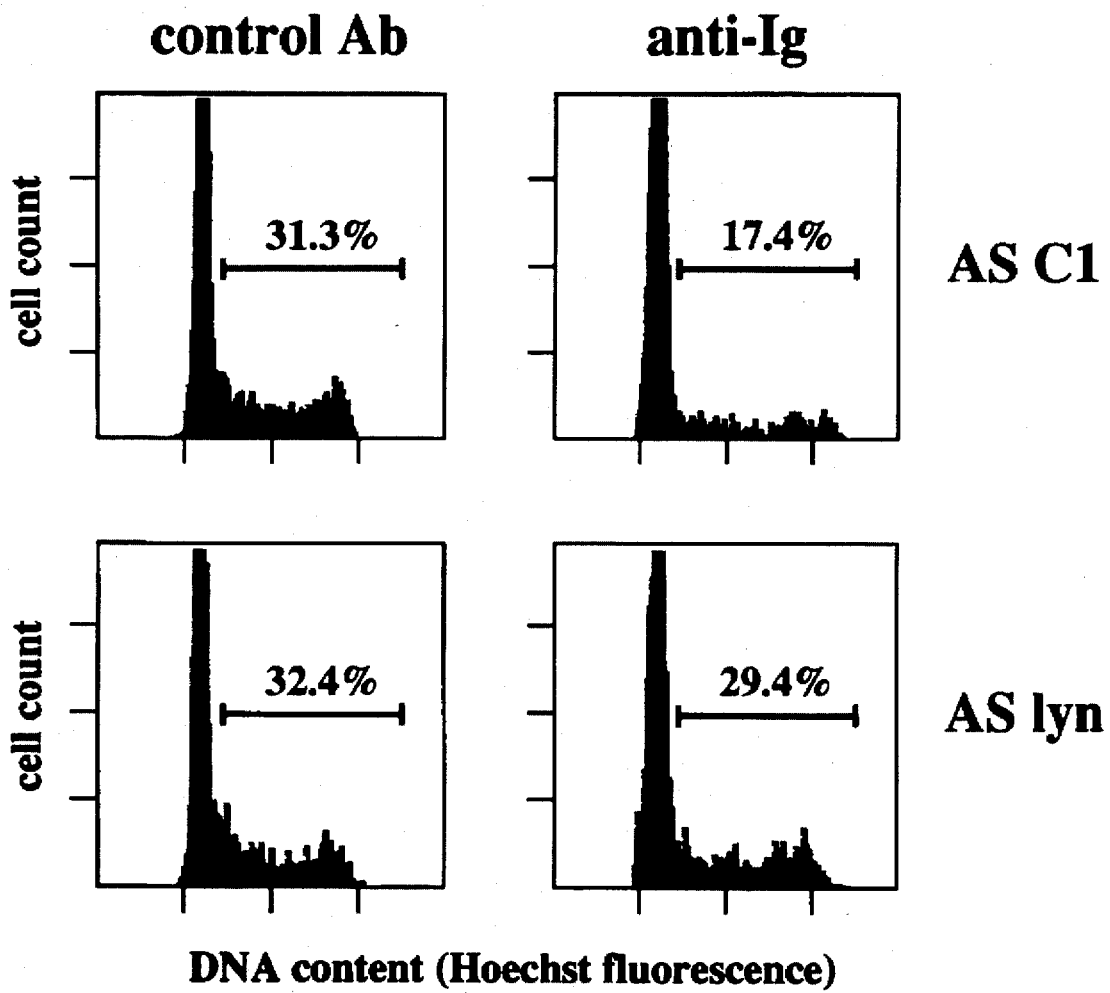
FIG. 7A. Anti-Ig antibodies induce cell cycle arrest and apoptosis in BCL$_1$.3B3 cells in vitro as shown by flow cytometric analysis of membrane integrity and DNA content. BCL$_1$.3B3 cells were treated with either rabbit anti-ovalbumin (top row) or rabbit anti-BCL$_1$ idiotype (bottom row) and analyzed by flow cytometry for membrane integrity using 7-AAD and for DNA content using Hoechst 33342. Viable cells exclude 7-AAD and bind intermediate to high amounts of Hoechst dye, including cells in the G$_0$/G$_1$ (colored red) and S/G$_2$/M (colored green) phases of the cell cycle. Apoptotic cells (colored black) have relatively low Hoechst fluorescence primarily due to induced DNA fragmentation, and most show a loss of membrane integrity (7-AAD$^+$). Cells in transition between viable and apoptotic are depicted in yellow. The percent of cells that are apoptotic is indicated in the upper right hand corner of 7-AAD vs. Hoechst fluorescence plots (left panels). Hoechst fluorescence gating only on viable cells is indicated in histograms (right panels), in which cells with a 1 n DNA content (G$_0$ or G$_1$ phases of the cell cycle) are shown in red and cells with a 1<n≦2 DNA content (S, G$_2$ or M phases of the cell cycle) in green. The percent of viable cells in the combined S, G$_2$ and M phases of the cell cycle is indicated in the upper right hand corner.
Figure 7B:
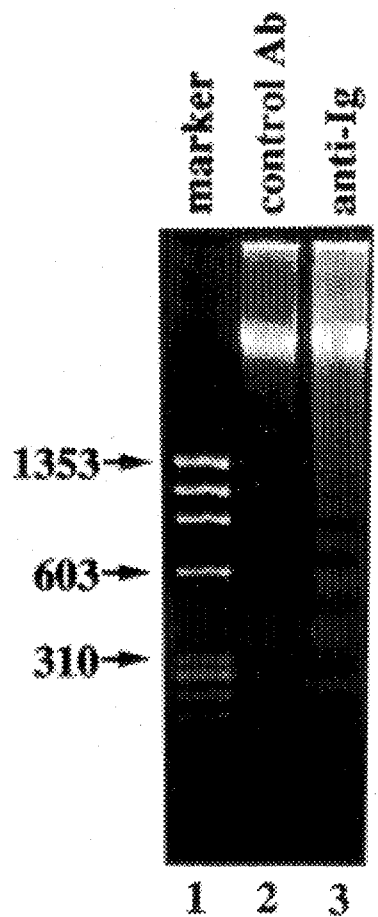
FIG. 7B. Anti-Ig antibodies induce cell cycle arrest and apoptosis in BCL$_1$.3B3 cells in vitro as shown by induction of nucleosomal ladder. BCL$_1$.3B3 cells were treated with either rabbit anti-ovalbumin (lane 2) or rabbit anti-mouse μ (lane 3) and total genomic DNA analyzed. Lane 1 contains φX174 HaeIII-digested DNA as a marker with representative sizes indicated in base pairs.

Treatment of in vitro adapted $BCL_1.3B3$ cell line with a variety of different antibodies against surface Ig results in the inhibition of cell growth as assessed by a decrease in the uptake of $^3$H-thymidine with an $IC_{50}$ of 1–4 µg/ml, whereas treatment with control antibodies, including rabbit and goat anti-ovalbumin and rat anti-Pgp1 (CD44; binds to 3B3.$BCL_1$ cells), had no effect. Two mechanisms contribute to this growth inhibition. $BCL_1.3B3$ cells treated with anti-Ig are induced into apoptosis, since a large proportion of treated cells lost both membrane integrity and DNA content as assessed by flow cytometry (FIG. 7a, bottom left panel), and since much of the DNA isolated from treated cells migrated as small discrete fragments the sizes of nucleosome multimers during gel electrophoresis (FIG. 7b, lane 3). In addition, flow cytometric analysis of DNA content revealed that many of the cells treated with anti-Ig were arrested in either the $G_0$ or $G_1$ phases of the cell cycle, since the number of viable cells in S, $G_2$ and M was half that of cells treated with control antibody (FIG. 7a, right panels).

Figure 8A:
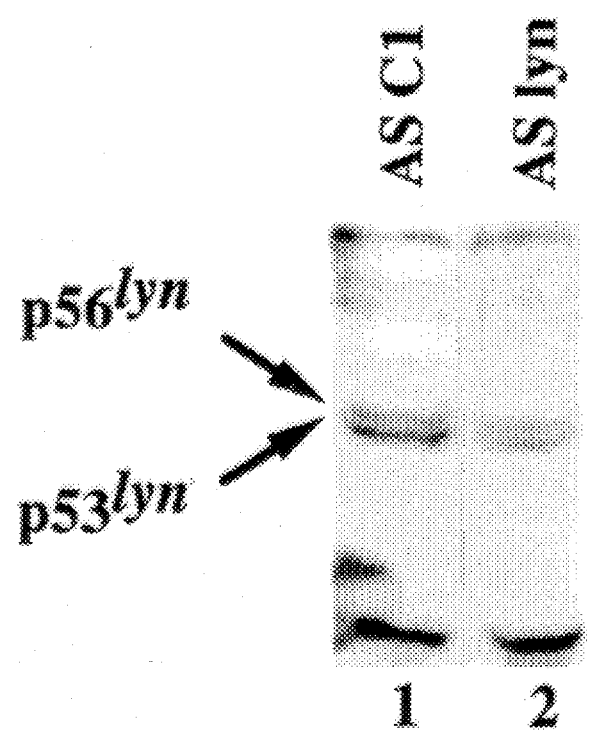
FIG. 8A. Antisense oligonucleotides to the lyn tyrosine kinase prevents growth arrest induced by anti-Ig by Immunoblot of BCL1.3B3 cells treated with antisense oligonucleotides. Cells were treated with antisense control (AS C1; lane 1) or antisense lyn (AS lyn; lane 2) for 24 hrs. and the lyn protein identified by immunoblotting. The two Lyn isoforms of 53 kD and 56 kD are indicated. Densitometry indicates that the level of Lyn protein is reduced to 52% of control samples by treatment with antisense lyn under these conditions.
Figure 8B:
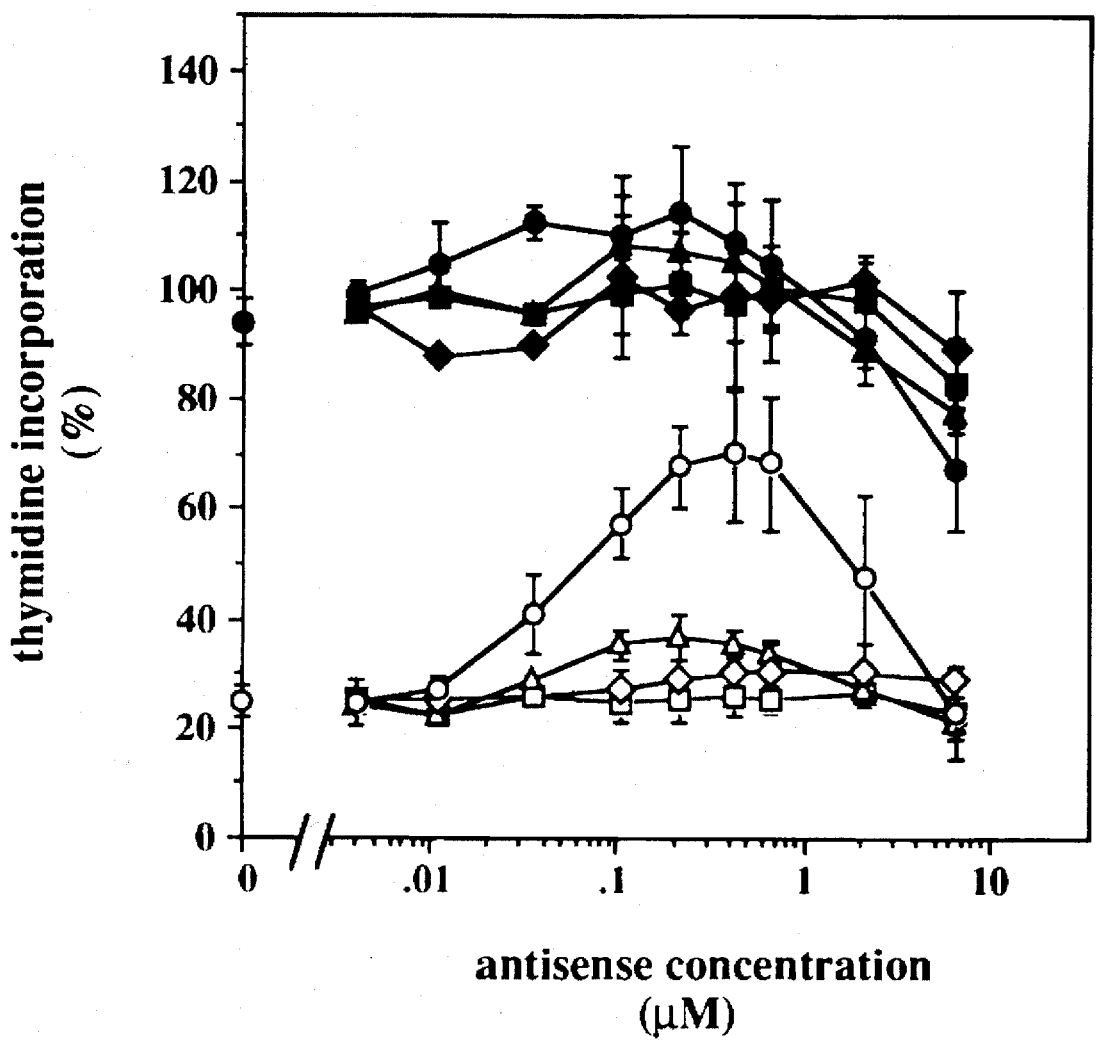
FIG. 8B. Antisense oligonucleotides to the lyn tyrosine kinase prevents growth arrest induced by anti-Ig by as shown by thymidine incorporation in the presence of antisense oligonucleotides. Cells were pre-treated with antisense oligonucleotides, either controls AS C1 (triangles), AS C2 (squares), AS C3 (diamonds) or with antisense lyn (circles) for 24 hrs. Either control antibodies (closed symbols) or anti-Ig antibodies (open symbols) were added and thymidine incorporation measured. Thymidine incorporation is given as the percent of incorporation in cells treated with medium alone. Results are a pool of five different experiments using either rabbit anti-mouse μ or goat anti-mouse μ as anti-Ig reagents, and rabbit anti-ovalbumin or goat anti-rabbit Ig as control antibodies. Error bars represent ±one standard deviation.

To examine the role of lyn in these signaling phenomena, the level of Lyn protein was depleted by treatment with phosphorothioate-modified antisense oligonucleotides (FIG. 8a), and the effect on cellular responses to cross-linking of mIg was evaluated. Moderate concentrations of antisense lyn had no effect on the growth of $BCL_1.3B3$ cells in the presence of control antibodies (FIG. 8b). However, these levels of antisense lyn dramatically reversed the growth inhibitory effect of anti-Ig on $BCL_1.3B3$ (FIG. 8b, open circles), in some cases up to 85% of control values. Several control antisense oligonucleotides had no effect on anti-Ig mediated growth inhibition. At high concentrations, all of the antisense oligonucleotides had non-specific toxic effects. This toxic effect is a result of the thiol modification since oligos with the same sequence and different modifications also reversed anti-Ig induced growth arrest without detectable toxicity.

Figure 9:
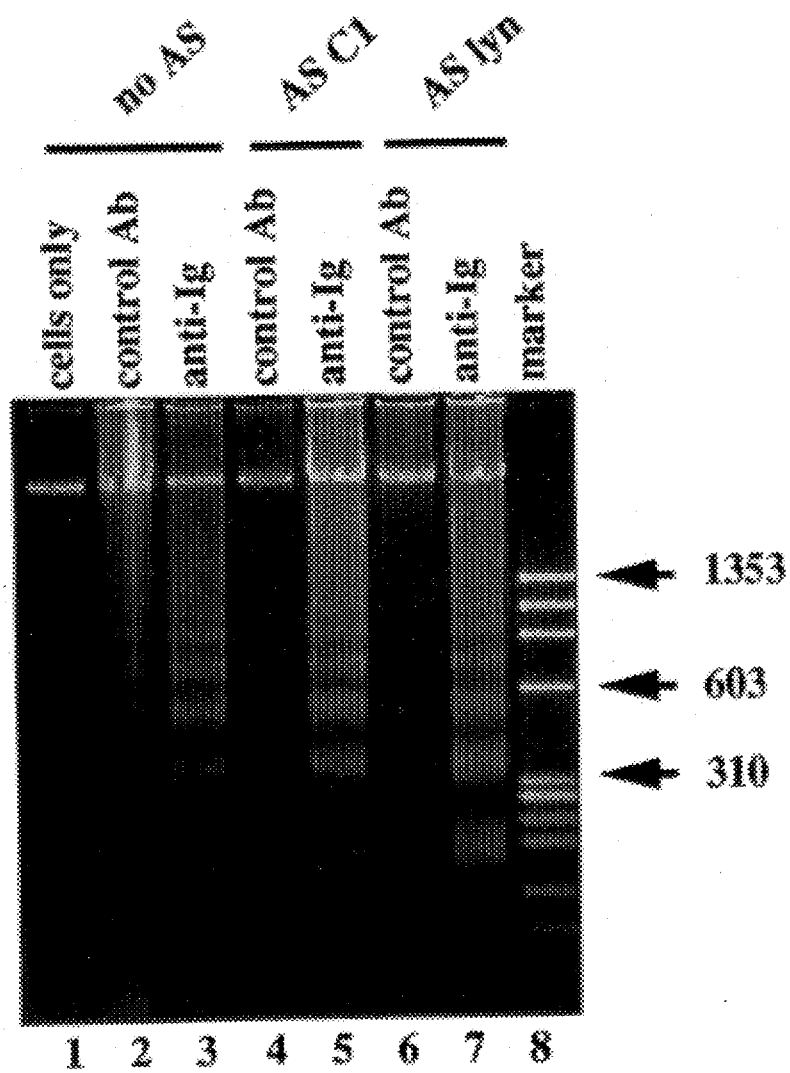
FIG. 9. Antisense lyn abrogates anti-Ig induced cell cycle arrest but not apoptosis as shown by nucleosomal ladder analysis. DNA was isolated from $BCL_1$.3B3 cells incubated in the absence of antisense oligonucleotides (lanes 1,2,3), or with AS C1 control (lanes 4 and 5) or AS lyn (lanes 6 and 7), and subsequently challenged with control antibody (rabbit anti-ovalbumin, lanes 2, 4, 6) or anti-Ig antibody (rabbit anti-$BCL_1$ idiotype, lanes 3, 5, 7). Sizes of selected DNA marker fragments (lane 8) are indicated.

The reversal of growth arrest suggested that Lyn might play a role in signaling cell cycle arrest, apoptosis or both. In the presence of control antisense, anti-Ig reduced the number of cells in the S, $G_2$ and M phases of the cell cycle (FIG. 9a, second row, right panel), to levels similar to those described in FIG. 7. On the other hand, pre-incubation with antisense lyn completely abrogated the inhibitory effect of anti-Ig on cell cycle progression (fourth row, right panel). In contrast, preincubation with antisense lyn had no significant effect on the induction of apoptosis by anti-Ig as assessed by flow cytometry (compare left panels of second and fourth rows) or by DNA laddering (FIG. 9b, compare lane 5 to lane 7).

The question arises as to whether this mechanism is peculiar to this cell line or whether it represents a more generalized phenomenon of cell cycle control through signal transduction in B lymphomas. Cross-linking of mIg on a human Burkitt's lymphoma cell line (Daudi) induces a two-fold reduction in the percent of viable cells in the S phase of the cell cycle (Table 9), as observed with $BCL_1.3B3$ cells. Pre-treatment of cells with two different lyn antisense oligonucleotide reagents results in either a partial (AS hulyn1) or a complete (AS hulyn2) abrogation of cell cycle arrest induced by anti-Ig (Table 9). Anti-Ig also induces apoptosis in Daudi; as with $BCL_1.3B3$, the level of apoptosis is not affected by lyn antisense treatment.

The inventors have recently demonstrated that cross-linking of another cell surface molecule, CD19, induces cell cycle arrest in Daudi cells. Since recent data have demonstrated an interaction between CD19 and Lyn, the role of Lyn in CD19-mediated signaling was investigated using antisense depletion. Once again, pre-treatment with the two different lyn antisense reagents resulted in either a partial or complete reversal of anti-CD19-mediated cell cycle arrest (Table 9).

TABLE 9

Antisense lyn abrogates cell cycle arrest induced by anti-Ig or anti-CD19 in human Daudi cells

| | Viable cells in S phase (% "cells only" control) | | | | |
|---|---|---|---|---|---|
| Treatment | No antisense | ASC1 | AS hulyn1 | ASC4 | AS hulyn2 |
| anti-ova (control) | 101 ± 3.8 | 88.6 ± 18 | 90.8 ± 16 | 100 ± 4.1 | 99.9 ± 1.6 |
| anti-Ig | 59.4 ± 9.5 | 59.8 ± 21 | 75.9 ± 6.6 | 59.0* | 100 ± 1.4 |
| anti-CD19 (HD-37) | 56.8 ± 2.1 | 57.5 ± 1.6 | 73.5 ± 0.1 | 56.0* | 97.5 ± 3.5 |

Daudi cells were suspended in growth medium to $0.7 \times 10^6$ cells/ml and treated with or without antisense oligonucleotides (as indicated) at a final concentration of 5 µM for 24 hrs. Cells were treated with either goat anti-human IgM, HD-37, or goat anti-ovalbumin and incubation continued for an additional 24 hrs. before analysis of DNA content by 7-AAD and Hoechst fluorescence. The percent of viable cells in the S phase of the cell cycle was calculated and compared with the percent of cells in SW phase for cells in medium alone ("cells only"). Values represent the average of two experiments ± one standard deviation, except that values indicated with * represent a single determination.

The major findings to emerge from these studies are: 1) anti-Ig treatment induces both cell cycle arrest and apoptosis in the mouse B cell lymphoma, $BCL_1.3B3$; 2) the Lyn tyrosine kinase is critical for signaling cell cycle arrest, but is apparently not required for signaling apoptosis in $BCL_1.3B3$; and 3) the Lyn tyrosine kinase is critical for signaling cell cycle arrest in the human Daudi lymphoma initiated through both mIg and CD19.

The induction of growth arrest, apoptosis and cell cycle arrest following treatment with anti-Ig has been reported for several B cell lines, including WEHI-231 and CH31 (Nossal, et al. (1992), Yao and Scott (1993)). Anti-Ig induces apoptosis and a reduction in the number of cells in the S, $G_2$ and M phases of the cell cycle in $BCL_1.3B3$ cells as well. The inventors interpret this latter effect as the induction of cell cycle arrest. However, an alternative explanation is that the induced apoptosis preferentially depletes cells in the S, $G_2$ and M phases. Several findings support the interpretation that anti-Ig induces authentic cell cycle arrest: 1) antisense lyn pre-treatment completely reverses the loss of S, $G_2$ and M phase cells without affecting apoptosis; 2) the relative levels of apoptosis and cell cycle arrest vary for different anti-Ig antibody preparations (manuscript in preparation); and 3) apoptotic cells can be observed as early as 2 hrs after antibody treatment, whereas cell cycle effects are only observed after 8 hrs. The relatively late onset of cell cycle effects argues for a block in early $G_1$.

These results also indicate that the pathways leading to cell cycle arrest and apoptosis are at least partially independent. The antisense experiments demonstrate that the Lyn tyrosine kinase is required to transduce a signal for cell cycle arrest initiated by cross-linking of mIg. Yet signaling per se can still occur in Lyn-depleted cells since apoptosis is induced to the same degree as in cells with their full complement of Lyn. Thus, the signal transduction cascade which originates from a single event (interaction with surface Ig) may rapidly bifurcate into two different pathways, the apoptosis pathway and the cell cycle arrest pathway, the latter requiring the Lyn tyrosine kinase. Alternatively, the concentration of Lyn required for apoptosis may be much lower than that required for induction of cell cycle arrest. The inventors favor the former explanation because there is evidence in other B cell lines that the signal for apoptosis is transduced through another of the Ig-associated tyrosine kinases, Blk. Taken together the data suggest that the different tyrosine kinases which associate with mIg control independent signal transduction pathways. A role for the other kinases in signaling cell cycle arrest however, is not excluded. Hence, activation of Lyn may initiate a cascade of protein phosphorylations in which Lyn activates Blk which activates Fyn, etc. However, the inability of anti-Ig to affect cell cycle progression in cells which have reduced levels of Lyn indicates that these other Ig-associated tyrosine kinases are insufficient to signal cell cycle arrest in the absence of Lyn.

Depletion of the Lyn protein by antisense requires that pre-existing protein is degraded during the treatment period. It is unclear how a two fold reduction in the level of Lyn protein could have such a profound effect on the ability of anti-Ig to induce cell cycle arrest. However, the level of Lyn protein which is physically associated with mIg may be lower than suggested by immunoblotting due to competition from the other src-family tyrosine kinases for the limited number of binding sites on the Ig-associated molecules IgM$\alpha$, Ig$\beta$ and Ig$\gamma$. In addition, cross-linking of mIg induces a rapid degradation of pre-existing Lyn protein; thus the two-fold reduction observed by antisense treatment alone may be an underestimate of the total effect in anti-Ig treated cells. The possibility that antisense lyn affects Ig-mediated cell cycle arrest in a non-specific manner seems unlikely since the inventors have not seen this type of effect with four other phosphorothioate reagents with similar base compositions and melting temperatures, and since antisense lyn reagents with different chemical modifications produce the same effect.

The relative contribution of cell cycle arrest and apoptosis to the induction of tumor dormancy in vivo is not known. While cell cycle progression in dormant lymphoma cells is reduced, there is still a portion of the population that is cycling (Yefenof, et al. (1993)). Since the proportion of dormant lymphoma cells in the spleen is stable for many months, it is likely that apoptosis is balancing residual cell division. The identification of Lyn as a critical player in cell cycle arrest but not apoptosis provides a new tool that will allow determination of the relative roles played by each of these processes.

The results indicate that the Lyn tyrosine kinase is also critical for the signaling of cell cycle arrest initiated by cross-linking of CD19. As there is evidence that CD19 is physically associated with the mIg complex, anti-CD19 antibodies might induce cell cycle arrest through the mIg complex. However, the facts that anti-CD19 can induce cell cycle arrest without apoptosis (Ghetie, et al. (1994)), in contrast to anti-Ig, and that Lyn is directly associated with CD19 (van Noesel, et al. (1993)) suggest that signal transduction might occur directly through CD19. Thus, the Lyn tyrosine kinase may initiate cell cycle arrest in response to two different cell surface molecules, mIg and CD19.

The activation of the Lyn kinase is probably not sufficient to impart a cell cycle arrest phenotype. Two types of B cell lines have been identified; those like BCL$_1$.3B3 that respond to mIg cross-linking by growth arrest and those like CH12 and A20-3 which do not. However, both classes of cell lines express equivalent levels of lyn mRNA, but show differential expression of the other kinases lck, blk and fyn, Thus, the growth response to Lyn activation may depend on the presence of other associated kinases, or signaling through other receptors. Nonetheless, these results demonstrate that without Lyn, cell cycle arrest signaling is not observed either from mIg or CD19.

EXAMPLE V

Human Immunotherapy Treatment Protocols

This example is concerned with human treatment protocols using the combination of immunotoxins disclosed above. It is proposed that anti-CD22 and anti-CD19 combined immunotoxin treatment will be of use in the clinical treatment of various human diseases and disorders in which B cells play a role. It is considered to be particularly useful tool in anti-tumor therapy, for example, in treating patients with refractory non-Hodgkin's lymphoma.

Methods of treating such patients using a single immunotoxin have already been formulated, for example, see Vitetta et al., *Cancer Res.*, 51:4052, 1991, incorporated herein by reference. It is contemplated that such methods may be straightforwardly adapted for use with the anti-CD22 immunotoxin/anti-CD19 combination described herein. As discussed above, the therapeutic agents could be administered either simultaneously or at distinct times. One may therefore employ either a pre-mixed pharmacological composition or "cocktail" of the therapeutic agents, or alternatively, employ distinct aliquots of the agents from separate containers.

The various elements of conducting a clinical trial, including patient treatment and monitoring, will be known to those of skill in the art in light of the present disclosure. The following information is being presented as a general guideline for use in establishing immunotoxin clinical trials.

It is contemplated that patients chosen for the study would have failed to respond to at least one course of conventional therapy and had to have objectively measurable disease as determined by physical examination, laboratory techniques, or radiographic procedures. Such patients should also have no history of allergy to mouse immunoglobulin or ricin, and any chemotherapy should be stopped at least 2 weeks before entry into the study.

In regard to immunotoxin administration, it is considered that certain advantages will be found in the use of an indwelling central venous catheter with a triple lumen port. The combination of, or distinct, immunotoxins should be filtered, for example, using a 0.22 µm filter, and diluted appropriately, such as with saline, to a final volume of 100 ml. Before use, the test sample should also be filtered in a similar manner, and its concentration assessed before and after filtration by determining the $A_{280}$. The expected recovery should be within the range of 87 to 99%, and adjustments for protein loss can then be accounted for.

The immunotoxins may be administered over a period of approximately 4 hours, with each patient receiving 2 to 6 infusions of combined or separate immunotoxins at 48-h intervals. Administration can also be performed by a steady rate of infusion over a 4–8 day period. The infusion given at any dose level should be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of immunotoxin should be administered to groups of patients until approximately 60% of patients showed unacceptable Grade III or IV toxicity in any category. Doses that are ⅔ of this value could be defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of immunotoxin and antibodies against the antibody and toxin components of the immunotoxin. Immunological analyses of sera, using any standard assay such as, for example, an ELISA or RIA, will allow the pharmacokinetics and clearance of each of the immunotherapeutic agents to be evaluated.

To evaluate the anti-tumor responses, it is contemplated that the patients should be examined at 48 hours to 1 week and again at 30 days after the last infusion. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days. Blood and bone marrow samples should also be evaluated histologically and by flow cytometry when disease was present in these sites.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement. Similarly, a mixed response may be defined by a reduction of the product of perpendicular diameters of all measurable lesions by 50% or greater 1 month after treatment, with progression in one or more sites.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Anderson K. C., Bates M. P., Slaughenhoupt B. L., Pinkus G. S., Schlossman S. F., Nadler L. M., *Blood*, 63:1424, 1984.

Bradbury L E, Kansas G S, Levy S, Evans R L, Tedder T F: The CD19/CD21 Signal transducing complex of human B lymphocytes includes the target of antiproliferative antibody-1 and leu-13 molecules. J Immunol 149:2841, 1992.

Brown S L, Miller R A, Horning S J, Czerwinski D, Hart S M, McElderry R, Basham T, Warnke R A, Merigan T C, Levy R: Treatment of B-cell lymphomas with anti-idiotype antibodies alone and in combination with alpha interferon. Blood 73(3):651, 1989.

Bzixeras E, Kroemer G, Cuende E, Marquez C, Bosca L, Martinez J E A, Martinez-A C: Signal transduction pathways involved in B-cell induction. Immunol Rev 132:5, 1993.

Byers, V. S., Baldwin R. W., *Immunology*, 65:329–335, 1988.

Byers, V. S., Rodvien, R., Grant, K., Durrant, L. G., Hudson, K. H., Baldwin, R. W., and Scannon, P. J., *Cancer Res.*, 49:6153–6160, 1989.

Callard R E, Rigley K P, Smith S H, Thurstan S, Shields J G: CD19 regulation of human B cell responses: B cell proliferation and antibody secretion are inhibited or enhanced by ligation of the CD19 surface glycoprotein depending on the stimulating signal used. J Immunol 148 (10):2983, 1992.

Cambier J C, Bedzyk W, Campbell K, Chien N, Friedrich J, Harwood A, Jensen W, Pleiman C, Clark M R: The B-cell antigen receptor: structure and function of primary, secondary, and Tertiary and Quaternary Components. Immunological Reviews 132:85, 1993.

Campana D., Janossy G., Bofill M., Trejdosiewicz L. K., Ma D., Hoffbrand A. V., Mason D. Y., LeBacq A-M., Forster H. K., *J. Immunol.*, 134:1524, 1985.

Carter R H, Tuveson D A, Park D J, Rhee S G, Fearon D T: The CD19 complex of lymphocytes-B—activation of phospholipase-C by a protein tyrosine kinase-dependent pathway that can be enhanced by the membrane IgM complex. J Immunol 147:3663, 1991.

DeFranco A L: Tyrosine phosphorylation and the mechanism of signal transduction by the B-lymphocyte antigen receptor. Eur J Biochem 210:381, 1992.

DeRie M. A., Schumacher T. N. M., VanSchijndel G. M. W., VanLier R. A. W., Miedema F., *Cell Immunol.*, 118:368, 1989.

Dörken, B. Schwarz, E., Feller, A. C., Hammerling, G., Hunstein, W., *Verh. Dtsch. Ges. Path.*, 67:65, 1983.

Dörken B., Moldenhauer G., Pezzutto A., Schwartz R., Feller A., Kiesel S., Nadler L. M., *J. Immunol.*, 136:4470, 1986.

Durandy A, Brousse N, Rozenberg F, Basile G D, Fischer A M, Fischer A: Control of human B cell tumor growth in severe combined immunodeficiency mice by monoclonal anti-B cell antibodies. J Clin Invest 90:945, 1992.

Dyer M J S, Hale G, Hayhoe F G J, Waldmann H: Effects of CAMPATH-1 antibodies in vivo in patients with lymphoid malignancies: influence of antibody isotype. Blood 73:1431, 1989.

Dyke R J, McBride H, George A J T, Hamblin T J, Stevenson F K: Idiotypic vaccination against B-cell lymphoma leads to dormant tumor. Cell Immunol 132:70, 1991.

Ehrlich, *The Collected Papers of Paul Ehrlich*, Ed. F. Himmelweit, Vol. 3, Pergamon, Elmsford, N.Y., 1960.

Fulton, R. J., Uhr, J. W., and Vitetta, E. S. *J. Immunol.*, 136:3103–3109, 1986.

Ghetie M-A., May R. D., Till M., Uhr J. W., Ghetie V., Knowles P. P., Relf M., Brown A., Wallace P. M., Janossy G., Amlot P., Vitetta E. S., Thorpe P. E., *Cancer Res.*, 48:2610, 1988 a.

Ghetie V., Ghetie M-A., Uhr J. W., Vitetta E. S., *J. Immunol. Methods*, 112:267, 1988b.

Ghetie M-A., Richardson J., Tucker T., Jones D., Uhr J. W., Vitetta E. S., *Int. J. Cancer*, 45:481, 1990.

Ghetie, M-A. Richardson J., Tucker T., Jones D., Uhr J. W., Vitetta E. S., *Cancer Res.* 51:5876, 1991.

Ghetie, M.-A., Picker, L. J., Richardson, J. A., Tucker, K., Uhr, J. W. & Vitetta, E. S. (1994) *Blood* 83, 1–9 (in press).

Goding J W: Production of monoclonal antibodies. New York, Academic Press, 1983.

Golay J T, Crawford D H: Pathways of human B-lymphocyte activation blocked by B-cell specific monoclonal antibodies. Immunol 62:279, 1987.

Grossbard M. L., Freedman A. S., Ritz J., Coral F., Goldmacher V. S., Eliseo L., Spector N., Dear K., Lambert J. M., Blattler W. A., Taylor J. A., Nadler L. M., *Blood*, 79:576, 1992.

Groux H, Torpier G, Monte D, Mouton Y, Capron A, Ameisen J C: Activation-induced death by apoptosis in CD4+ T-cells from human immunodeficiency virus-infected asymptomatic individuals. J Exp Med 175:331, 1992.

Hara H., Luo Y., Haruta Y., Seon B. K., *Cancer Res*, 48:4673, 1988.

Hebell T, Ahearn J M, Fearon D T: Suppression of the immune response by a soluble complement receptor of B lymphocytes. Science 254:102, 1991.

Hekman A., Honselaar A., Vuist W. M. J., Sein J. J., Rodenhuis S., ten Bokkel Huinink W. W., Somers R., Rumke Ph., Melief C. J. M., *Cancer Immunol. Immunother.*, 32:364, 1991.

Hertler, A. A., Schlossman, D. M., and Borowitz, M. J., *J. Biol. Response Modif.*, 7:97–113, 1988.

Ishigami T., Kim K. M., Horiguchi Y., Higaki Y., Hata D., Heike T., Katamura K., Mayumi M., Mikawa H., *J Immunol* 148:360, 1992.

Jansen B., Uckun F. M., Jaszcz W. B., Kersey J. H., *Cancer Res.*, 52:406, 1992.

Katz F. E., Janossy G., Cumber A., Ross W., Blacklock H. A., Tax W., Thorpe P. E., *Br. J. Haematol.*, 67:407, 1987.

Knapp, W., Dorken, B., Gilks, W. R., Rieber, E. P., Schmidt, R. E., Stein, H., von dem Borne, A. E. G. Kr. (eds) Leucocyte Typing IV. 1989. Oxford University Press, Oxford, U.K.

Knowles, P. P., and Thorpe, P. E. *Anal. Biochem.*, 160:440–443, 1987.

Kozmik Z, Wang S, Dorfler P, Adams B, Busslinger M: The promoter of the CD19 gene is a target for the B-cell-specific transcription factor BSAP. Mol Cell Biol 12:2662, 1992.

Krolick, K. A., Villemez, C., Isakson, P., Uhr, J. W., and Vitetta, E. S. *Proc. Natl. Acad. Sci.* (USA), 77:5419–5423, 1980.

Laemmli U. K., *Nature*, 227:680, 1970.

Law D A, Gold M R, DeFranco A L: Examination of B lymphoid cell lines for membrane immunoglobulin-stimulated tyrosine phosphorylation and src-family tyrosine kinase and mRNA expression. Mol Immunol 29:917, 1993.

Ledbetter J A, Rabinovitch P S, June C H, Song C W, Clark E A, Uckun F M: Antigen-independent regulation of cytoplasmic calcium in B cells with a 12-kDa B-cell growth factor and anti-CD19. Proc Natl Acad Sci (USA) 85:1897, 1988.

Li, J-L., Shen, G-L., Ghetie, M-A., May, R. D., Till, M., Ghetie, V., Uhr, J. W., Janossy, G., Thorpe, P. E., Amlot, P., Vitetta, E. S., *Cell Immunol*, 118:85–89, 1989.

Matsumoto A K, Martin D R, Carter R H, Klickstein L B, Ahearn J M, Fearon D T: Functional dissection of the CD21/CD19/TAPA-1/Leu-13 complex of B lymphocytes. J Exp M ed 178:1407, 1993.

May R. D., Vitetta E. S., Moldenhauer G., Dörken B., *Cancer Drug Delivery*, 3(4):261, 1986.

Meeker T C, Lowder J, Maloney D G, Miller R A, Thielemans K, Warnke R, Levy R: A clinical trial of anti-idiotype therapy for B cell malignancy. Blood 65:1349, 1985.

Moldenhauer, G., Dörken, B., Schwartz, R., Pezzutto, A., Hammerling, G. J., In *Leukocyte Typing II*, Eds. E. L. Reinherz, B. F. Haynes, L. M. Nadler & I. D. Bernstein I. D., Springer-Verlag, New York, 1986, p 97–107.

Nadler, L. M., In *Leukocyte Typing II*, Eds. E. L. Reinherz, B. F. Haynes, L. M. Nadler & I. D. Bernstein I. D., Springer-Verla g, New York, 1986, p 3.

Nossal, G. J. V. (1992) *Adv. Immunol.* 52, 283–331.

Oratz, R., Speyer, J. L., Wernz, J. C., Hochster, H., Myers, M., Mischak, R., and Spitler, L. E. *J. Biol. Response Modif.*, 9:345–354, 1990.

Pezzutto A., Dörken B., Feller A., Moldenhauer G., Schwartz R., Wernet P., Thiel E., Hunstein W., In *Leukocyte Typing II*, Eds. E. L. Reinherz, B. F. Haynes, L. M. Nadler & I. D. Bernstein I. D., Springer-Verlag, New York, 1986, p 391.

Pezzutto A., Dorken B., Rabinovitch P. S., Ledbetter J. A., Moldenhauer G., Clark E. A., *J. Immunol.*, 138:2793, 1987.

Press O. W., Vitetta E. S., Martin, P. J., *Immunol. Let.*, 14:37, 1986.

Press O W, Appelbaum F, Ledbetter J A, Martin P J, Zarling J, Kidd P, Thomas E D: Monoclonal antibody 1F5 (anti-CD20) serotherapy of human B cell lymphomas. Blood 69:584, 1987.

Rigley K. P., Callard R. E., *Eur. J. Immunol.*, 21:535, 1991.

Shen G-L., Li J-L., Ghetie M-A., Ghetie V., May R. D., Till M., Brown A. N., Relf M., Knowles P., Uhr J. W., Janossy G., Amlot P., Vitetta E. S., Thorpe P. E., *Int. J. Cancer*, 42:792, 1988.

Spiegelberg H. L., Weigle W. O., *J. Exp. Med.*, 121:323, 1965.

Spitler, L. E., de Rio, M., Khentigan, A., Wedel, N. I., Brophy, N. A., Miller, L. L., Harkonen, W. S., Rasendorf, L. L., Lee, H. M., Mischak, R. P., Kawahata, R. T., Stoudemire, J. B., Fradkin, L. B., Bautita, E. E., and Scannon, P. J. *Cancer Res.*, 47:1717–1723, 1987.

Thorpe P. E., Detre S. I., Foxwell B. M. J., Brown A. N. F., Skilleter D. N., Wilson G., Forrester J. A., Stirpe F., *Eur. J. Biochem.*, 147:197, 1985.

Trucco M, De Petris S: Determination of equilibrium binding parameters of monoclonal antibodies specific for cell surface antigens, in Lefkovits I, Pernis B (eds): Immunological Methods. Vol. II, New York, Academic Press, 1981, p 1.

Uckun F M, Jaszcz W, Ambrus J L, Fauci A S, Gajl-Peczalska K, Song C W, Rostaing-Capaillon O, Myers D E, Waddick K, Ledbetter J A: Detailed studies on expression and function of CD19 surface determinant by using B43 monoclonal antibody and the clinical potential of anti-CD19 immunotoxins. Blood 71:13, 1988.

Vitetta E. S. Fulton R. J., May R. D., Till M., Uhr., *Science*, 238:1098, 1987.

Vitetta E. S., Stone M., Amlot P., Fay J., May R., Till M., Newman J., Clark P., Collins R., Cunningham D., Ghetie V., Uhr J. W., Thorpe P. E. *Cancer Res.*, 51:4052, 1991.

Vuist W. M. J., Von Buitenen F., De Rie M. A., Hekman A., Rumke P., Melief C. J. M., *Cancer Res.*, 49:3783, 1989.

Weiner, L. M., O'Dwyer, J., Kitson J., Comis, R. L., Frankel, A. E., Bauer, R. J., Konrad, M. S., and Groves, E. S. *Cancer Res.*, 49:4062–4067, 1989.

Yao X R, Scott D W: Expression of protein tyrosine kinases in the Ig complex of anti-mu-sensitive and anti-mu-resistant B-cell lymphomas: role of the p55blk kinase in signaling growth arrest and apoptosis. Immunological Reviews 132:163, 1993.

Yefenof E, Picker L J, Scheuermann R E, Tucker T F, Vitetta E S, Uhr. J. W.: Cancer Dormancy: Isolation and characterizati on of dormant lymphoma cells. Proc Natl Acad Sci (USA) 90:1829, 1993.

---

What is claimed is:

1. A method for delivering a toxin to a $CD22^+$ B cell, comprising contacting said $CD22^+$ B cell with a CD22-binding immunotoxin and a CD19-binding antibody that binds to the epitope bound by the antibody HD37, or a CD19-binding fragment or immunotoxin conjugate thereof, in a combined amount effective to kill said $CD22^+$ cell.

2. The method of claim 1, wherein said CD22-binding immunotoxin comprises the CD22-binding antibody UV22-1, UV22-2, HD6, or RFB4, or a CD22-binding fragment thereof.

3. The method of claim 2, wherein said CD22-binding immunotoxin comprises the CD22-binding antibody RFB4, or a CD22-binding fragment thereof.

4. The method of claim 1, wherein said CD22-binding immunotoxin comprises a univalent CD22-binding antibody fragment thereof.

5. The method of claim 4, wherein said univalent CD22-binding antibody fragment is an Fab' or Fab'Fc fragment.

6. The method of claim 1, wherein said CD19-binding antibody is the CD19-binding antibody HD37 or 4G7.

7. The method of claim 1, wherein said CD19-binding antibody fragment is a CD19-binding $F(ab')_2$ antibody fragment.

8. The method of claim 1, wherein said CD19-binding immunotoxin comprises a univalent CD19-binding fragment.

9. The method of claim 8, wherein said univalent CD19-binding fragment is an Fab' or Fab'Fc fragment.

10. The method of claim 1, wherein the toxin component of the immunotoxin is the A chain portion of ricin, abrin, modeccin, botulina or diphtheria toxin.

11. The method of claim 10, wherein the toxin is ricin A chain.

12. The method of claim 11, wherein the ricin A chain is deglycosylated ricin A chain.

13. The method of claim 1, wherein said CD22-binding immunotoxin and said CD19-binding antibody, fragment or immunotoxin are administered to a human subject.

14. The method of claim 13, wherein said CD22-binding immunotoxin and said CD19-binding antibody, fragment or immunotoxin are administered simultaneously.

15. The method of claim 13, wherein said CD22-binding immunotoxin and said CD19-binding antibody, fragment or immunotoxin are administered consecutively.

16. The method of claim 13, wherein the human subject has leukemia or non-Hodgkin's lymphoma.

17. The method of claim 13, wherein the human subject is the recipient of a transplant or xenograft.

18. A method for potentiating the B cell cytotoxicity of a CD22-binding immunotoxin comprising contacting B cells with a CD22-binding immunotoxin and a CD19-binding antibody that binds to the epitope bound by the antibody HD37, or a CD19-binding fragment or immunotoxin conjugate thereof, in a combined amount effective to kill said B cells.

19. A pharmacological composition comprising a therapeutically effective combination of a CD22-binding immunotoxin and a CD19-binding antibody that binds to the epitope bound by the antibody HD37, or a fragment or immunotoxin conjugate thereof.

20. The composition of claim 19, wherein said CD22-binding immunotoxin comprises the CD22-binding antibody RFB4, or a CD22-binding fragment thereof.

21. The composition of claim 19, wherein said CD19-binding antibody is the CD19-binding antibody HD37.

22. The composition of claim 21, wherein said CD19-binding antibody is the CD19-binding antibody 4G7.

23. The composition of claim 19, wherein the toxin component of the immunotoxin is ricin A chain.

24. The composition of claim 23, wherein the ricin A chain is deglycosylated ricin A chain.

25. The composition of claim 19, suitable for parenteral administration.

26. A kit for use in delivering a toxin to a B cell, comprising:

(a) a CD22-binding immunotoxin composition and a CD19-binding antibody composition that comprises an antibody that binds to the epitope bound by the antibody HD37, or a CD19-binding fragment or immunotoxin thereof; and (b) a means for containing said compositions.

27. The kit of claim 26, wherein said compositions are pharmacological compositions.

28. The kit of claim 26, further defined as comprising a single container.

29. The kit of claim 26, further defined as comprising distinct containers.

30. A method for delivering a toxin to a $CD22^+$ B cell, comprising contacting said $CD22^+$ B cell with a CD22-binding immunotoxin and a CD19-binding antibody that binds to the epitope bound by the antibody HD37, or a CD19-binding fragment or conjugate thereof, in a combined amount effective to kill said $CD22^+$ cell.

31. A pharmacological composition comprising a therapeutically effective combination of a CD22-binding immunotoxin and a CD19-binding antibody that binds to the epitope bound by the antibody HD37, or a CD19-binding fragment thereof.

32. A kit for use in delivering a toxin to a B cell, comprising:
   (a) a CD22-binding immunotoxin composition and CD19-binding antibody composition that comprises an antibody that binds to the epitope bound by the antibody HD37, or a CD19-binding fragment thereof; and
   (b) a means for containing said compositions.

* * * * *